United States Patent
Reitblat et al.

(10) Patent No.: US 9,510,875 B2
(45) Date of Patent: Dec. 6, 2016

(54) SYSTEMS AND METHODS FOR PERCUTANEOUS SPINAL FUSION

(71) Applicant: Stryker Spine, Cestas (FR)

(72) Inventors: Abram Reitblat, Monroe, NY (US); Joshua Stein, Hoboken, NJ (US); Amir Ali Sharifi-Mehr, Bloomingdale, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 135 days.

(21) Appl. No.: 14/206,431

(22) Filed: Mar. 12, 2014

(65) Prior Publication Data

US 2014/0277206 A1 Sep. 18, 2014

Related U.S. Application Data

(60) Provisional application No. 61/783,098, filed on Mar. 14, 2013.

(51) Int. Cl.
*A61B 17/70* (2006.01)

(52) U.S. Cl.
CPC ....... *A61B 17/7085* (2013.01); *A61B 17/7074* (2013.01); *A61B 17/7083* (2013.01); *A61B 17/7091* (2013.01); *A61B 17/708* (2013.01)

(58) Field of Classification Search
CPC ......... A61B 17/7076; A61B 17/7083–17/7091
(Continued)

(56) References Cited

U.S. PATENT DOCUMENTS

| | | |
|---|---|---|
| 3,788,318 A | 1/1974 | Kim et al. |
| 3,789,852 A | 2/1974 | Kim et al. |

(Continued)

FOREIGN PATENT DOCUMENTS

| | | |
|---|---|---|
| DE | 3711091 | 10/1988 |
| DE | 4238339 A1 | 5/1994 |

(Continued)

OTHER PUBLICATIONS

Extended European Search Report for Application No. EP14159945 dated Jul. 1, 2014.

(Continued)

*Primary Examiner* — Nicholas Plionis
(74) *Attorney, Agent, or Firm* — Lerner, David, Littenberg, Krumholz & Mentlik, LLP

(57) ABSTRACT

A system for percutaneous spinal fusion may include two spaced apart blades connected together by a coupling such that the blades define a percutaneous pathway from a skin incision to an implanted pedicle fastener. The coupling may be c-shaped and may have at least one flexible tab for engaging one or more holes along the length of the blades. If one of the blades becomes disconnected from the pedicle fastener, a supplemental access device may be provided comprising a tubular body having a channel therein for receiving the other of the blades. If both of the blades become disconnected, a supplemental access device may be provided comprising a gripping member received within a locking member. The gripping member may have two legs engageable with the pedicle fastener, and the locking member may move along the gripping member to prevent the legs from disengaging the pedicle fastener.

23 Claims, 20 Drawing Sheets

(58) Field of Classification Search
USPC .................................................... 606/86 A
See application file for complete search history.

(56) References Cited

U.S. PATENT DOCUMENTS

| | | | |
|---|---|---|---|
| 3,892,232 A | 7/1975 | Neufeld |
| 4,083,370 A | 4/1978 | Taylor |
| 4,269,184 A | 5/1981 | Montgomery |
| 4,350,151 A | 9/1982 | Scott |
| 4,409,968 A | 10/1983 | Drummond |
| 4,411,259 A | 10/1983 | Drummond |
| 4,448,191 A | 5/1984 | Rodnyansky et al. |
| 4,449,532 A | 5/1984 | Storz |
| 4,474,046 A | 10/1984 | Cook |
| 4,545,374 A | 10/1985 | Jacobson |
| 4,562,832 A | 1/1986 | Wilder et al. |
| 4,611,581 A | 9/1986 | Steffee |
| 4,653,481 A | 3/1987 | Howland et al. |
| 4,790,297 A | 12/1988 | Luque |
| 4,817,587 A | 4/1989 | Janese |
| 4,862,891 A | 9/1989 | Smith |
| 4,887,595 A | 12/1989 | Heinig et al. |
| 4,899,729 A | 2/1990 | Gill et al. |
| 4,913,134 A | 4/1990 | Luque |
| 4,957,495 A | 9/1990 | Kluger |
| 4,984,564 A | 1/1991 | Yuen |
| 5,010,879 A | 4/1991 | Moriya et al. |
| 5,027,793 A | 7/1991 | Engelhardt et al. |
| 5,035,232 A | 7/1991 | Lutze et al. |
| 5,125,396 A | 6/1992 | Ray |
| 5,139,487 A | 8/1992 | Baber |
| 5,171,279 A | 12/1992 | Mathews |
| 5,183,464 A | 2/1993 | Dubrul et al. |
| 5,195,541 A | 3/1993 | Obenchain |
| 5,197,971 A | 3/1993 | Bonutti |
| 5,242,443 A | 9/1993 | Kambin |
| 5,293,863 A | 3/1994 | Zhu et al. |
| 5,295,994 A | 3/1994 | Bonutti |
| D346,217 S | 4/1994 | Sparker et al. |
| 5,312,417 A | 5/1994 | Wilk |
| 5,357,983 A | 10/1994 | Mathews |
| 5,360,431 A | 11/1994 | Puno et al. |
| 5,373,860 A | 12/1994 | Catone |
| 5,377,667 A | 1/1995 | Patton et al. |
| 5,381,788 A | 1/1995 | Matula et al. |
| 5,395,317 A | 3/1995 | Kambin |
| 5,409,488 A | 4/1995 | Ulrich |
| 5,425,732 A | 6/1995 | Ulrich |
| 5,439,464 A | 8/1995 | Shapiro |
| 5,454,365 A | 10/1995 | Bonutti |
| 5,464,011 A | 11/1995 | Bridge |
| 5,480,440 A | 1/1996 | Kambin |
| 5,490,409 A | 2/1996 | Weber |
| 5,496,322 A | 3/1996 | Mathews |
| 5,545,228 A | 8/1996 | Kambin |
| 5,569,248 A | 10/1996 | Mathews |
| 5,569,290 A | 10/1996 | McAfee |
| 5,584,887 A | 12/1996 | Kambin |
| 5,591,165 A | 1/1997 | Jackson |
| 5,601,562 A | 2/1997 | Wolf et al. |
| 5,601,590 A | 2/1997 | Bonutti et al. |
| 5,624,442 A | 4/1997 | Mellinger et al. |
| 5,658,286 A | 8/1997 | Sava |
| 5,707,359 A | 1/1998 | Bufalini |
| 5,720,751 A | 2/1998 | Jackson |
| 5,728,097 A | 3/1998 | Mathews |
| 5,741,261 A | 4/1998 | Moskovitz et al. |
| 5,743,907 A | 4/1998 | Asher et al. |
| 5,746,720 A | 5/1998 | Stouder, Jr. |
| 5,762,629 A | 6/1998 | Kambin |
| 5,772,594 A | 6/1998 | Barrick |
| 5,792,044 A | 8/1998 | Foley et al. |
| 5,795,289 A | 8/1998 | Wyttenbach |
| 5,814,046 A | 9/1998 | Hopf et al. |
| 5,882,344 A | 3/1999 | Stouder, Jr. |
| 5,885,291 A | 3/1999 | Moskovitz et al. |
| 5,885,292 A | 3/1999 | Moskovitz et al. |
| 5,891,147 A | 4/1999 | Moskovitz et al. |
| 5,902,231 A | 5/1999 | Foley et al. |
| RE36,221 E | 6/1999 | Breard et al. |
| 5,928,139 A | 7/1999 | Koros et al. |
| 5,938,662 A | 8/1999 | Rinner |
| 5,944,658 A | 8/1999 | Koros et al. |
| 5,954,635 A | 9/1999 | Foley et al. |
| 5,957,888 A | 9/1999 | Hinchliffe |
| 5,961,499 A | 10/1999 | Bonutti et al. |
| 5,964,761 A | 10/1999 | Kambin |
| 5,976,146 A | 11/1999 | Ogawa et al. |
| 6,007,487 A | 12/1999 | Foley et al. |
| 6,015,409 A | 1/2000 | Jackson |
| 6,033,406 A | 3/2000 | Mathews |
| 6,035,691 A | 3/2000 | Lin et al. |
| 6,036,692 A | 3/2000 | Burel et al. |
| 6,080,156 A | 6/2000 | Asher et al. |
| 6,090,113 A | 7/2000 | Le Couedic et al. |
| 6,123,707 A | 9/2000 | Wagner |
| 6,127,597 A | 10/2000 | Beyar et al. |
| 6,152,871 A | 11/2000 | Foley et al. |
| 6,159,179 A | 12/2000 | Simonson |
| 6,162,170 A | 12/2000 | Foley et al. |
| 6,175,758 B1 | 1/2001 | Kambin |
| 6,176,823 B1 | 1/2001 | Foley et al. |
| 6,183,472 B1 | 2/2001 | Lutz |
| 6,187,000 B1 | 2/2001 | Davison et al. |
| 6,197,002 B1 | 3/2001 | Peterson |
| 6,200,322 B1 | 3/2001 | Branch et al. |
| 6,206,822 B1 | 3/2001 | Foley et al. |
| 6,206,826 B1 | 3/2001 | Mathews et al. |
| 6,217,509 B1 | 4/2001 | Foley et al. |
| 6,226,548 B1 | 5/2001 | Foley et al. |
| 6,235,028 B1 | 5/2001 | Brumfield et al. |
| 6,287,313 B1 | 9/2001 | Sasso |
| 6,332,780 B1 | 12/2001 | Traxel et al. |
| 6,338,730 B1 | 1/2002 | Bonutti et al. |
| 6,358,266 B1 | 3/2002 | Bonutti |
| 6,371,968 B1 | 4/2002 | Kogasaka et al. |
| 6,425,859 B1 | 7/2002 | Foley et al. |
| 6,475,218 B2 | 11/2002 | Gournay et al. |
| 6,485,518 B1 | 11/2002 | Cornwall et al. |
| 6,506,151 B2 | 1/2003 | Estes et al. |
| 6,520,907 B1 | 2/2003 | Foley et al. |
| 6,524,320 B2 | 2/2003 | DiPoto |
| 6,530,926 B1 | 3/2003 | Davison |
| 6,530,929 B1 | 3/2003 | Justis et al. |
| 6,558,386 B1 | 5/2003 | Cragg |
| 6,558,390 B2 | 5/2003 | Cragg |
| 6,562,046 B2 | 5/2003 | Sasso |
| 6,575,979 B1 | 6/2003 | Cragg |
| 6,596,008 B1 | 7/2003 | Kambin |
| 6,605,095 B2 | 8/2003 | Grossman |
| 6,607,530 B1 | 8/2003 | Carl et al. |
| 6,613,050 B1 | 9/2003 | Wagner et al. |
| 6,648,888 B1 | 11/2003 | Shluzas |
| 6,652,553 B2 | 11/2003 | Davison et al. |
| 6,660,006 B2 | 12/2003 | Markworth et al. |
| 6,692,434 B2 | 2/2004 | Ritland |
| 6,692,473 B2 | 2/2004 | St. Cyr et al. |
| 6,723,095 B2 | 4/2004 | Hammerslag |
| 6,740,089 B2 | 5/2004 | Haider |
| 6,740,090 B1 | 5/2004 | Cragg et al. |
| 6,746,449 B2 | 6/2004 | Jones et al. |
| 6,749,614 B2 | 6/2004 | Teitelbaum et al. |
| 6,770,074 B2 | 8/2004 | Michelson |
| 6,790,210 B1 | 9/2004 | Cragg et al. |
| 6,793,656 B1 | 9/2004 | Mathews |
| 6,800,084 B2 | 10/2004 | Davison et al. |
| 6,811,558 B2 | 11/2004 | Davison et al. |
| 6,821,277 B2 | 11/2004 | Teitelbaum |
| 6,837,891 B2 | 1/2005 | Davison et al. |
| 6,849,064 B2 | 2/2005 | Hamada |
| 6,875,212 B2 | 4/2005 | Shaolian et al. |
| 6,899,713 B2 | 5/2005 | Shaolian et al. |
| 6,923,811 B1 | 8/2005 | Carl et al. |
| 6,929,647 B2 | 8/2005 | Cohen |

(56) References Cited

U.S. PATENT DOCUMENTS

| | | |
|---|---|---|
| 6,964,667 B2 | 11/2005 | Shaolian et al. |
| 7,008,422 B2 | 3/2006 | Foley et al. |
| 7,008,424 B2 | 3/2006 | Teitelbaum |
| 7,011,660 B2 | 3/2006 | Sherman et al. |
| 7,083,621 B2 | 8/2006 | Shaolian et al. |
| 7,160,300 B2 | 1/2007 | Jackson |
| 7,188,626 B2 | 3/2007 | Foley et al. |
| 7,250,052 B2 | 7/2007 | Landry et al. |
| 7,261,714 B2 | 8/2007 | Richelsoph |
| 7,306,603 B2 | 12/2007 | Boehm, Jr. et al. |
| 7,491,218 B2 | 2/2009 | Landry et al. |
| 7,758,617 B2 | 7/2010 | Iott et al. |
| 7,811,288 B2 | 10/2010 | Jones et al. |
| 7,842,073 B2 | 11/2010 | Richelsoph et al. |
| 7,927,360 B2 | 4/2011 | Pond, Jr. et al. |
| 7,955,355 B2 | 6/2011 | Chin |
| 8,002,798 B2 | 8/2011 | Chin et al. |
| 8,105,361 B2 | 1/2012 | Anderson et al. |
| 8,157,809 B2 | 4/2012 | Butters et al. |
| 8,177,817 B2 | 5/2012 | Fallin |
| 8,192,440 B2 | 6/2012 | Jones et al. |
| 2001/0011170 A1 | 8/2001 | Davison et al. |
| 2001/0027320 A1 | 10/2001 | Sasso |
| 2001/0029353 A1 | 10/2001 | Peterson |
| 2001/0049498 A1 | 12/2001 | Davison et al. |
| 2001/0049527 A1 | 12/2001 | Cragg |
| 2001/0053915 A1 | 12/2001 | Grossman |
| 2002/0016583 A1 | 2/2002 | Cragg |
| 2002/0045904 A1 | 4/2002 | Fuss et al. |
| 2002/0068975 A1 | 6/2002 | Teitelbaum et al. |
| 2002/0082598 A1 | 6/2002 | Teitelbaum |
| 2002/0082600 A1 | 6/2002 | Shaolian et al. |
| 2002/0107519 A1 | 8/2002 | Dixon et al. |
| 2002/0116006 A1 | 8/2002 | Cohen |
| 2002/0161367 A1 | 10/2002 | Ferree |
| 2002/0161368 A1 | 10/2002 | Foley et al. |
| 2002/0173796 A1 | 11/2002 | Cragg |
| 2002/0198526 A1 | 12/2002 | Shaolian et al. |
| 2003/0004517 A1 | 1/2003 | Anderson |
| 2003/0060824 A1 | 3/2003 | Viart et al. |
| 2003/0060826 A1 | 3/2003 | Foley et al. |
| 2003/0073998 A1 | 4/2003 | Pagliuca et al. |
| 2003/0083688 A1 | 5/2003 | Simonson |
| 2003/0139648 A1 | 7/2003 | Foley et al. |
| 2003/0195518 A1 | 10/2003 | Cragg |
| 2003/0199871 A1 | 10/2003 | Foley et al. |
| 2003/0199872 A1 | 10/2003 | Markworth et al. |
| 2003/0199884 A1 | 10/2003 | Davison et al. |
| 2003/0204189 A1 | 10/2003 | Cragg |
| 2003/0208202 A1 | 11/2003 | Falahee |
| 2003/0225408 A1 | 12/2003 | Nichols et al. |
| 2003/0229353 A1 | 12/2003 | Cragg |
| 2004/0006341 A1 | 1/2004 | Shaolian et al. |
| 2004/0006344 A1 | 1/2004 | Nguyen et al. |
| 2004/0034351 A1 | 2/2004 | Sherman et al. |
| 2004/0039384 A1 | 2/2004 | Boehm et al. |
| 2004/0059333 A1 | 3/2004 | Carl et al. |
| 2004/0082954 A1 | 4/2004 | Teitelbaum et al. |
| 2004/0082960 A1 | 4/2004 | Davison |
| 2004/0082961 A1 | 4/2004 | Teitelbaum |
| 2004/0087950 A1 | 5/2004 | Teitelbaum |
| 2004/0092934 A1 | 5/2004 | Howland |
| 2004/0093001 A1 | 5/2004 | Hamada |
| 2004/0106934 A1 | 6/2004 | Grossman |
| 2004/0133201 A1 | 7/2004 | Shluzas et al. |
| 2004/0138662 A1 | 7/2004 | Landry et al. |
| 2004/0143265 A1 | 7/2004 | Landry et al. |
| 2004/0143268 A1 | 7/2004 | Falahee |
| 2004/0147928 A1 | 7/2004 | Landry et al. |
| 2004/0147936 A1 | 7/2004 | Rosenberg et al. |
| 2004/0147937 A1 | 7/2004 | Dunbar et al. |
| 2004/0162560 A1 | 8/2004 | Raynor et al. |
| 2004/0172022 A1 | 9/2004 | Landry et al. |
| 2004/0176763 A1 | 9/2004 | Foley et al. |
| 2004/0194791 A1 | 10/2004 | Sterman et al. |
| 2004/0215190 A1 | 10/2004 | Nguyen et al. |
| 2004/0215193 A1 | 10/2004 | Shaolian et al. |
| 2004/0236317 A1 | 11/2004 | Davison |
| 2004/0254576 A1 | 12/2004 | Dunbar et al. |
| 2004/0260287 A1 | 12/2004 | Ferree |
| 2004/0267275 A1 | 12/2004 | Cournoyer et al. |
| 2004/0267279 A1 | 12/2004 | Casutt et al. |
| 2005/0010220 A1 | 1/2005 | Casutt et al. |
| 2005/0010221 A1 | 1/2005 | Dalton |
| 2005/0021030 A1 | 1/2005 | Pagliuca et al. |
| 2005/0021031 A1 | 1/2005 | Foley et al. |
| 2005/0025771 A1 | 2/2005 | Wagner et al. |
| 2005/0033297 A1 | 2/2005 | Davison |
| 2005/0038432 A1 | 2/2005 | Shaolian et al. |
| 2005/0038434 A1 | 2/2005 | Mathews |
| 2005/0043741 A1 | 2/2005 | Michelson |
| 2005/0043742 A1 | 2/2005 | Bruneau et al. |
| 2005/0059969 A1 | 3/2005 | McKinley |
| 2005/0065515 A1 | 3/2005 | Jahng |
| 2005/0065517 A1 | 3/2005 | Chin |
| 2005/0070917 A1 | 3/2005 | Justis |
| 2005/0080418 A1 | 4/2005 | Simonson et al. |
| 2005/0085813 A1 | 4/2005 | Spitler et al. |
| 2005/0090822 A1 | 4/2005 | DiPoto |
| 2005/0090833 A1 | 4/2005 | DiPoto |
| 2005/0113833 A1 | 5/2005 | Davison |
| 2005/0124991 A1 | 6/2005 | Jahng |
| 2005/0131407 A1 | 6/2005 | Sicvol et al. |
| 2005/0131408 A1 | 6/2005 | Sicvol et al. |
| 2005/0131421 A1 | 6/2005 | Anderson et al. |
| 2005/0131422 A1 | 6/2005 | Anderson et al. |
| 2005/0137461 A1 | 6/2005 | Marchek et al. |
| 2005/0137593 A1 | 6/2005 | Gray et al. |
| 2005/0149022 A1 | 7/2005 | Shaolian et al. |
| 2005/0149035 A1 | 7/2005 | Pimenta et al. |
| 2005/0154389 A1 | 7/2005 | Selover et al. |
| 2005/0165396 A1 | 7/2005 | Fortin et al. |
| 2005/0171540 A1 | 8/2005 | Lim et al. |
| 2005/0182410 A1 | 8/2005 | Jackson |
| 2005/0192570 A1 | 9/2005 | Jackson |
| 2005/0228392 A1 | 10/2005 | Keyer et al. |
| 2005/0245928 A1 | 11/2005 | Colleran et al. |
| 2005/0251139 A1 | 11/2005 | Roh |
| 2005/0277934 A1 | 12/2005 | Vardiman |
| 2005/0277942 A1 | 12/2005 | Kullas et al. |
| 2006/0030839 A1 | 2/2006 | Park et al. |
| 2006/0030858 A1 | 2/2006 | Simonson et al. |
| 2006/0030861 A1 | 2/2006 | Simonson et al. |
| 2006/0036252 A1 | 2/2006 | Baynham et al. |
| 2006/0084980 A1 | 4/2006 | Melkent et al. |
| 2006/0111713 A1 | 5/2006 | Jackson |
| 2006/0111714 A1 | 5/2006 | Foley |
| 2006/0200132 A1 | 9/2006 | Chao et al. |
| 2006/0200135 A1 | 9/2006 | Sherman et al. |
| 2006/0217735 A1 | 9/2006 | MacDonald et al. |
| 2006/0247630 A1* | 11/2006 | Iott .............. A61B 17/701 606/86 A |
| 2006/0247658 A1 | 11/2006 | Pond et al. |
| 2006/0264934 A1 | 11/2006 | Fallin |
| 2006/0264962 A1 | 11/2006 | Chin et al. |
| 2006/0293680 A1 | 12/2006 | Jackson |
| 2007/0043359 A1 | 2/2007 | Altarac et al. |
| 2007/0083210 A1 | 4/2007 | Hestad et al. |
| 2007/0093824 A1 | 4/2007 | Hestad et al. |
| 2007/0233079 A1 | 10/2007 | Fallin et al. |
| 2008/0009864 A1 | 1/2008 | Forton et al. |
| 2008/0125789 A1 | 5/2008 | Butters et al. |
| 2008/0125817 A1 | 5/2008 | Arnett et al. |
| 2009/0099605 A1 | 4/2009 | Fallin et al. |
| 2009/0216328 A1 | 8/2009 | Birkmeyer et al. |
| 2009/0228053 A1 | 9/2009 | Kolb et al. |
| 2009/0228054 A1* | 9/2009 | Hoffman .......... A61B 17/7086 606/86 A |
| 2009/0228056 A1 | 9/2009 | Jackson |
| 2010/0137915 A1 | 6/2010 | Anderson et al. |
| 2010/0331901 A1 | 12/2010 | Iott et al. |
| 2011/0015678 A1 | 1/2011 | Jackson |
| 2011/0077692 A1 | 3/2011 | Jackson |
| 2011/0152940 A1 | 6/2011 | Frigg et al. |

(56) References Cited

U.S. PATENT DOCUMENTS

| | | |
|---|---|---|
| 2011/0238120 A1 | 9/2011 | Chin |
| 2011/0245884 A9 | 10/2011 | Brumfield et al. |
| 2012/0022594 A1 | 1/2012 | Walker et al. |
| 2012/0089191 A1 | 4/2012 | Altarac et al. |
| 2012/0109208 A1* | 5/2012 | Justis .......... A61B 17/7032 606/264 |
| 2012/0123477 A1 | 5/2012 | Landry et al. |
| 2012/0158070 A1 | 6/2012 | Jackson |
| 2012/0197302 A1 | 8/2012 | Fallin |

FOREIGN PATENT DOCUMENTS

| | | |
|---|---|---|
| DE | 29710979 U1 | 8/1997 |
| DE | 19726754 A1 | 2/1999 |
| DE | 10027988 | 1/2002 |
| EP | 0528177 | 2/1993 |
| EP | 0528562 | 2/1993 |
| EP | 0611116 | 8/1994 |
| EP | 0665731 | 8/1995 |
| EP | 1006888 | 6/2000 |
| EP | 1027988 | 8/2000 |
| EP | 1248568 | 10/2002 |
| EP | 1374786 | 1/2004 |
| EP | 1468652 | 10/2004 |
| EP | 1545355 | 6/2005 |
| JP | 2003-511190 A | 3/2003 |
| JP | 2006-504505 A | 2/2006 |
| SU | 839513 | 6/1981 |
| WO | 93/18722 | 9/1993 |
| WO | 94/09726 | 5/1994 |
| WO | 9514437 | 6/1995 |
| WO | 97/14457 | 4/1997 |
| WO | 9822030 A1 | 5/1998 |
| WO | 98/36785 | 8/1998 |
| WO | 98/38918 | 9/1998 |
| WO | 99/29242 | 6/1999 |
| WO | 99/51139 | 10/1999 |
| WO | 00/45720 | 8/2000 |
| WO | 01/12080 | 2/2001 |
| WO | 01/37744 | 5/2001 |
| WO | 01/41681 | 6/2001 |
| WO | 01/56479 | 8/2001 |
| WO | 01/60234 | 8/2001 |
| WO | 01/60262 | 8/2001 |
| WO | 01/60263 | 8/2001 |
| WO | 01/60270 | 8/2001 |
| WO | 01060232 | 8/2001 |
| WO | 01/95823 | 12/2001 |
| WO | 02/085217 | 10/2002 |
| WO | 03020110 | 3/2003 |
| WO | 03/028566 | 4/2003 |
| WO | 03/037170 | 5/2003 |
| WO | 03/057055 | 7/2003 |
| WO | 03/079914 | 10/2003 |
| WO | 03/088810 | 10/2003 |
| WO | 03/088878 | 10/2003 |
| WO | 2004004584 | 1/2004 |
| WO | 2004017847 | 3/2004 |
| WO | 2004021899 | 3/2004 |
| WO | 2004/028382 | 4/2004 |
| WO | 2004/037070 | 5/2004 |
| WO | 2004037074 | 5/2004 |
| WO | 2004041100 | 5/2004 |
| WO | 2004058045 | 7/2004 |
| WO | 2004/080318 | 9/2004 |
| WO | 2005018466 | 3/2005 |
| WO | 2005020832 A1 | 3/2005 |
| WO | 2005023123 | 3/2005 |
| WO | 2005032358 | 4/2005 |
| WO | 2005060534 A | 7/2005 |
| WO | 2005/072081 | 8/2005 |
| WO | 2005072081 | 8/2005 |
| WO | 2006036324 A2 | 4/2006 |
| WO | 2006/116662 | 11/2006 |
| WO | 2006/125029 | 11/2006 |
| WO | 2012091737 A1 | 7/2012 |

OTHER PUBLICATIONS

Bare Bones; Monthly Executive Summary, vol. 12, No. 1, p. 1-4, Jan. 2003.

Charles Hartjen; The Atavi System, Surgical Technique Brochure. Endius, p. 1-17, undated.

Communication from corresponding European Application, 06 76 0048, dated Sep. 29, 2009.

Diapason, Surgical Texchnique Catalog, Diapasan Spinal System, Jan. 2002.

Encore Spine; Degenerative System, Encore Surgical Product Brochure, p. 1-6, Oct. 2002.

Examination report from corresponding European Application, 06 76 0048, dated Aug. 20, 2008.

Kambin et al, "Percutaneous Posterolateral Lumbar Discectomy and Decompression with a 6.9-millimeter cannula", The Journal of Bone and Joint Surgery, pp. 822-831, Jul. 1991.

Kambin et al., Anterior Column Support for Failed Fusion, Revision Spine Surgery, pp. 589-600, from 1999.

Kambin, "Arthroscopic Microdiscectomy", The Journal of Arthroscopy, vol. 8, No. 3, pp. 287-295, 1992.

Kambin, "Arthroscopic Microdiskectomy", The Mount Sinai Journal of Medicine, vol. 58, No. 2, Mar. 1991, pp. 159-164.

Kambin, "Posterolateral Percutaneous suction-excision of herniated lumbar intervertebral discs", Clinical Orthopaedics and Related Research. No. 207, pp. 37-42, Jun. 1988.

Kambin, Arthroscopic Lumbar Intervertebral Fusion, Chapter 95, The Adult Spine, vol. 2, pp. 2037-2046, 1997.

Kambin, Minimally Invasive Techniques in Spinal Surgery Current Practice, Neurosurgical Focus, wwwspineuniversecom, 16 pages, printed Aug. 24, 2005.

Kambin, Posterolateral Percutaneous Lumbar Discectomy and Decompression Arthroscopic Microdiscectomy, Section IV. pp. 67-100, 1991.

Kambin, Posterolateral Percutaneous Lumbar Interbody Fusion, Arthroscopic Microdiscectomy, pp. 117-121, 1991.

Kambin, The Role of Minimally Invasive Surgery in Spinal Disorders, Advance Operative Orthopedics, vol. 3, pp. 147-171, 1995.

Leu et al., Percutaneous Fusion of the Lumbar Spine, State of the Art Reviews, vol. 6, No. 3, pp. 593-604, Sep. 1992.

Maxcess; Decompression Surgical Technique. Nuvasive Creative Spine Technology Product Brochure, p. 1-16, undated.

Maxcess; XLIF 90° Surgical Technique. Nuvasive Creative Spine Technology Product Brochure, p. 1-26, 2005.

Moss Miami Surgical Texhnique, DePuy, 14 pages, 1998.

Nex-Link; Spinal Fixation System, Spinal Concepts Web Page information, 1 page.

Nuvasive; SpheRx DBR Minimally Disruptive FLxation, Nuvasive web page information, undated.

Office Action from U.S. Appl. No. 10/868,075, mailed Oct. 12, 2007.

Office Action from U.S. Appl. No. 10/868,075, mailed Mar. 24, 2008.

Office Action from U.S. Appl. No. 10/868,075, mailed Mar. 9, 2009.

Office Action from U.S. Appl. No. 11/178,035, mailed Mar. 4, 2009.

Office Action from U.S. Appl. No. 11/178,035, mailed May 1, 2008.

Office Action from U.S. Appl. No. 11/178,035, mailed Sep. 5, 2008.

Office Action from U.S. Appl. No. 11/202,487, mailed Dec. 9, 2008.

Office Action from Japanese Application No. 2008-55422 dated Sep. 2, 2011.

Office Action from U.S. Appl. No. 10/868,075, dated Sep. 18, 2008.

Office Action from U.S. Appl. No. 11/178,035, mailed Nov. 13, 2009.

Office Action from U.S. Appl. No. 11/202,487, dated Dec. 9, 2008.

Office Action from U.S. Appl. No. 11/202,487, mailed Aug. 5, 2009.

Office Action from U.S. Appl. No. 11/526,785, dated Jan. 8, 2009.

Office Action from U.S. Appl. No. 11/526,785, mailed Jan. 8, 2009.

Office Action from U.S. Appl. No. 11/526,785, mailed Sep. 3, 2009.

(56) References Cited

OTHER PUBLICATIONS

Office Action from U.S. Appl. No. 12/316,637, mailed Oct. 17, 2011.
Pathfinder; Minimally Invasive Pedicie Fixation System. Spinal Concepts Product Brochure p. 1-4, May 2003.
Pathfinder; Minimally invasive Spinal Fixation System and Surgical Technique. Spinal Concepts Product Brochure, p. 1-26, undated.
Smith and Nephew; 6.5mm and 4.0mm Cannulated Screws, Surgical Technique, p. 1-24, 1998.
Sofamor Danek; Eclipse CD Horizon Eclipse Implants and Instruments, Information from the Sofamor Danek Web page, p. 1-3, printed Mar. 29, 2005.
Sofamor Danek; Metrx, X-Tube, Refraction System; Sofamor Danek Web page information p. 1-2, printed Mar. 29, 2005.
Sofamor Danek; Sextant CD Horizon Sextant Rod Insertion System, Surgical Technique, Techniques, p. 1-29, 2003.
Spinal Concepts; Access Dilation Port, Spinal Concepts Web Page information 2 pages, 2004.
Synthes; MIRA for M.LS.S, Surgical Technique Brochure. Synthes, p. 1-7, undated.

\* cited by examiner

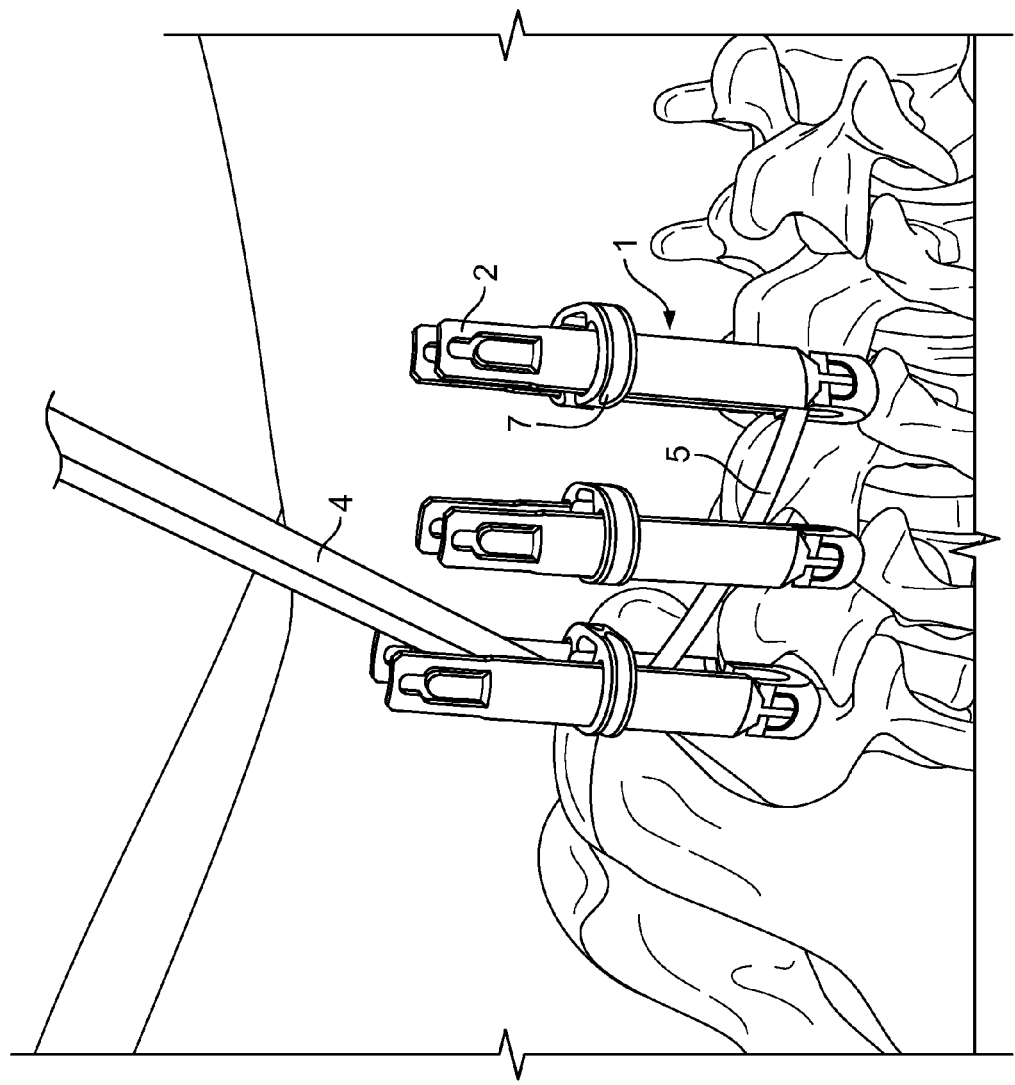

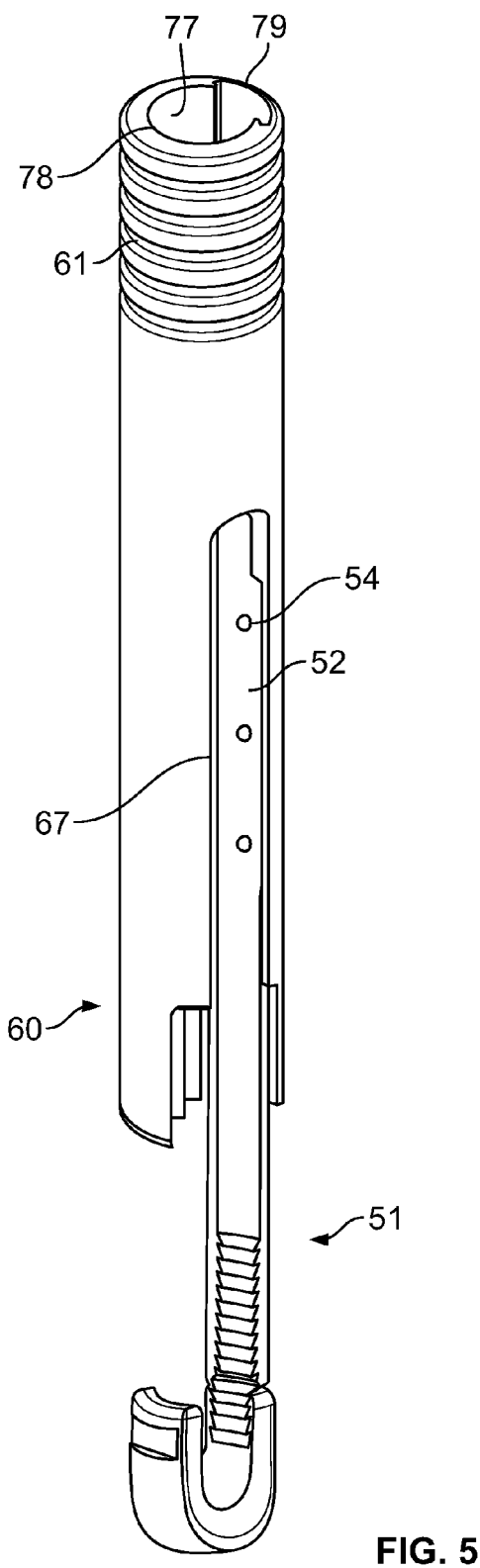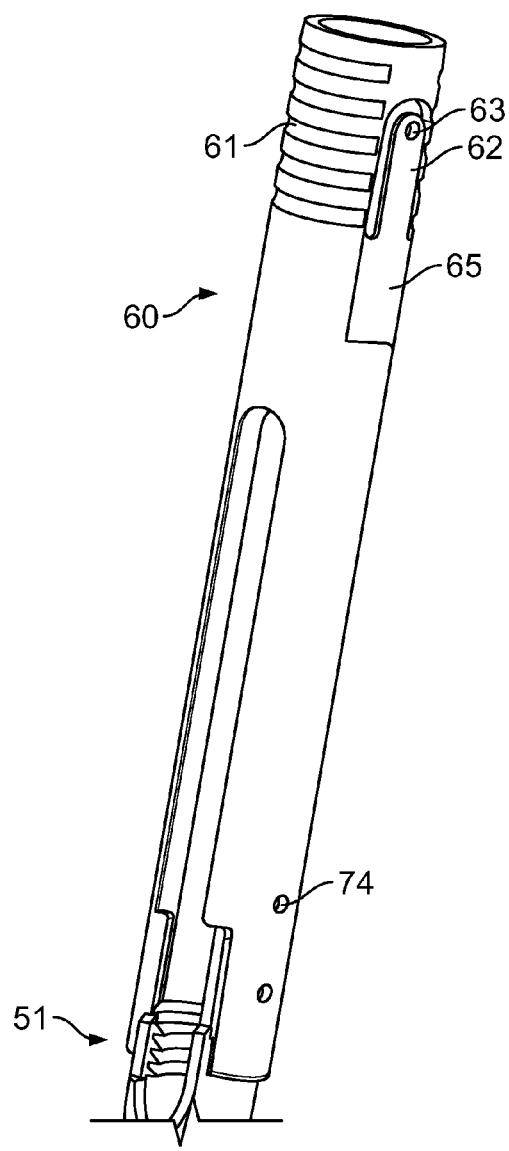
FIG. 5
FIG. 6A

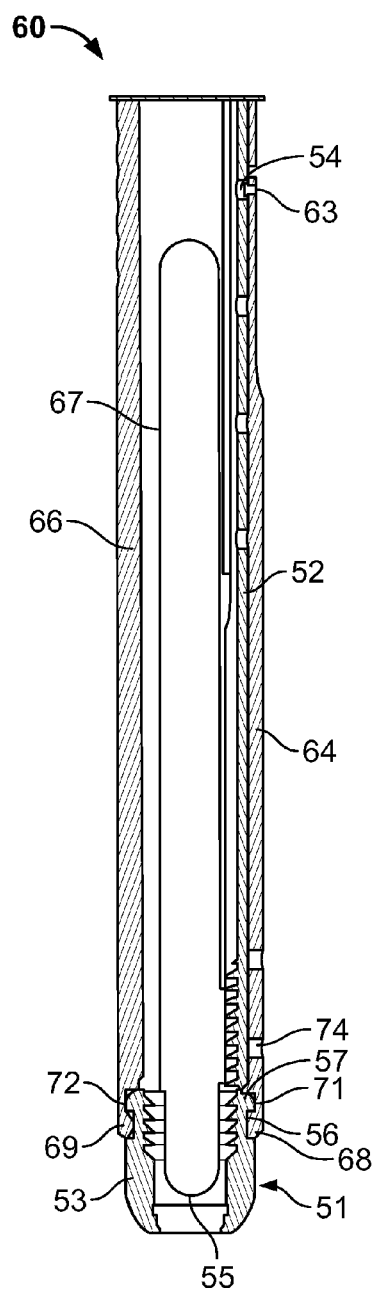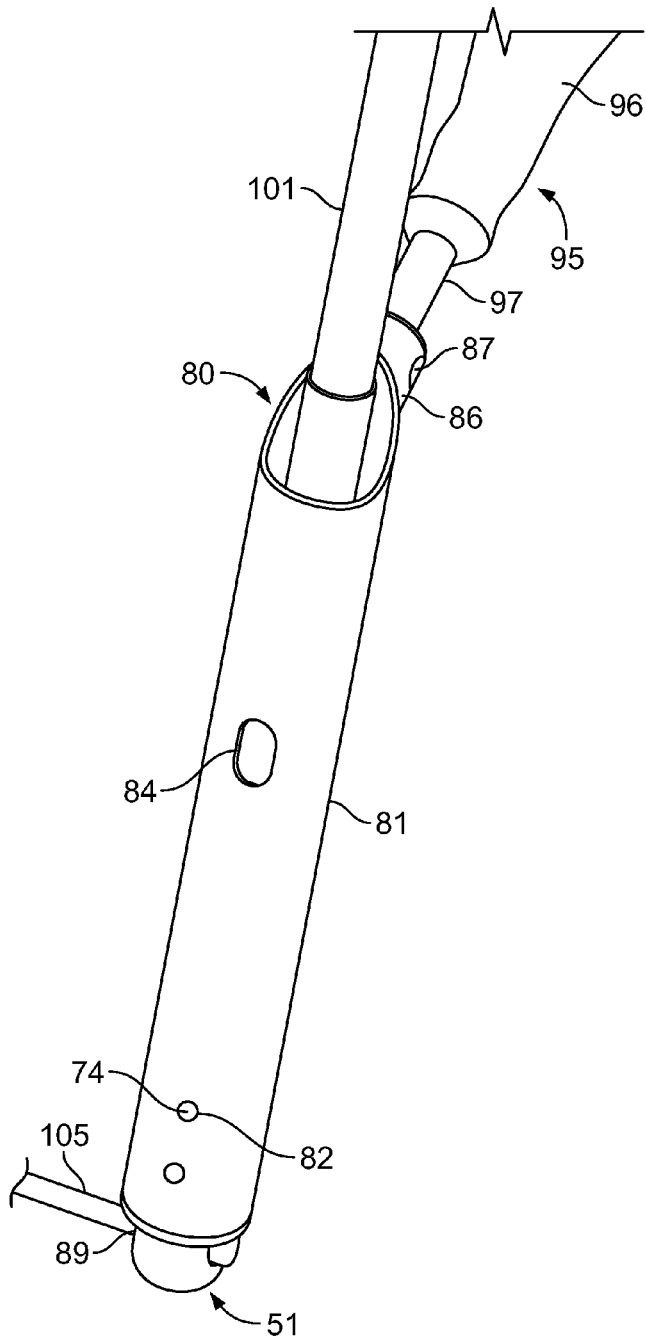
FIG. 6B
FIG. 7

SYSTEMS AND METHODS FOR PERCUTANEOUS SPINAL FUSION

CROSS-REFERENCE TO RELATED APPLICATIONS

This application claims the benefit of the filing date of U.S. Provisional Application No. 61/783,098 filed Mar. 14, 2013, the disclosure of which is hereby incorporated herein by reference.

BACKGROUND OF THE INVENTION

The present invention relates to systems and methods for the insertion of spinal fixation rods, or simply spinal rods or fixation rods, and in particular, to systems and methods for percutaneously guiding spinal fixation rods to a target location adjacent the spinal column.

Pedicle screw fixation systems have been in use for decades in order to fuse adjacent vertebral segments to improve spinal stability or correct certain spinal deformities. Older approaches for inserting these fixation systems involved open procedures, in which relatively large skin incisions were created to expose a substantial portion of the patient's spinal column, in order to allow for insertion of the pedicle screws and manipulation of spinal rods through openings in pedicle screws, such openings typically being in heads of the screws.

Over time, less invasive approaches have been developed. Typically, in such approaches, pedicle screws are inserted into the pedicles of selected vertebrae of a patient's spine through individual percutaneous incisions corresponding to the pedicle screws. Fixation or fusion rods are then inserted into the body through one of those incisions or through an additional incision adjacent the most cephalad or caudal pedicle screw, and the rod is positioned through openings in the heads of the pedicle screws to fix the relative positions of the pedicle screws through which the rod is inserted. In some such minimally invasive procedures, a percutaneous access device (e.g., a cannula or portal) is connected to each of the pedicle screws and extends through the respective percutaneous incision. Such percutaneous access devices provide a pathway through the tissue from each incision to the respective pedicle screw, in order to aid in the insertion of a spinal rod. Examples of such percutaneous access devices are described in commonly-assigned U.S. Pat. No. 7,955,355 ("the '355 patent") and U.S. Pat. No. 8,002,798 ("the '798 patent"), the entireties of which are hereby incorporated by reference herein as if fully set forth herein.

One example of a commercially used minimally invasive spinal fusion system is the MANTIS® Spinal System developed by Stryker Corporation, the assignee of the present application, and exemplified by the spinal fixation system shown in FIGS. 1A and 1B. As shown in those figures, blades 2 are connected to opposing sides of the heads 3 of pedicle screws implanted in respective vertebrae, such that the blades 2 extend posteriorly through respective incisions in the patient's skin and define pathways extending between each incision and the respective pedicle screw. In certain systems, the blades 2 may be separately formed from and detachably connectable to the pedicle screw heads 3, and, in other systems, the blades may be integrally formed with the pedicle screw heads 3 to form monolithic blade-screws. In the case of integrally formed blade-screws, the blades 2 may be connected to the pedicle screw heads 3 by frangible portions (e.g., reduced thickness portions, which may be defined by grooves formed in either or both of the interior and exterior surfaces of the blade-screws at the junction between the blades and the pedicle screw heads). Such frangible portions provide a location for the blades to be broken away from the pedicle screw heads when desired. With either form of the blades, a rigid ring 7 may be placed over and slid along each of the blades 2 until the rigid ring 7 abuts the skin of the patient. In this manner, the ring 7 may stabilize the spinal insertion system with respect to the skin and also provide rigidity to the spinal rod insertion system by maintaining the relative positioning of the blades 2 and resisting their disconnection from the pedicle screw heads 3. Similar blade and abutment ring structures are described in the '798 patent.

In the minimally invasive approach illustrated in FIGS. 1A and 1B, a rod insertion tool 4 is used to insert a fixation rod 5 into the body between the blades 2, which act to provide percutaneous pathways and help to guide the movement of the rod 5 to the desired position connecting the pedicle screw heads 3. Following insertion of the rod 5, the blades 2 are intentionally disconnected from the pedicle screw heads 3 and removed from the patient.

When using a blade-screw having blades integrally formed with a pedicle screw head, one or both of the blades can be broken at the respective one or both of the frangible connections between the blades and the screw head during insertion and manipulation of the rod 5, and even during insertion of the blade-screw. In such instances, the broken blade-screw needs to be replaced in order to provide a guide in which to insert the fixation rod 5, requiring dilation to retract the blade-screw. Thus, there is a need for systems and methods to guide the fixation rod without dilation and without requiring the use of a separate guide.

BRIEF SUMMARY OF THE INVENTION

One aspect of the present invention provides a method for restoring a percutaneous pathway to a pedicle fastener connected to a vertebra of a patient. The method according to this aspect of the invention desirably includes inserting a percutaneous access device into a body of a patient through an incision, such that the percutaneous access device desirably provides a first pathway extending from the incision to a head of a pedicle fastener connected to a vertebra of the patient. The method may also include removing at least a portion of the percutaneous access device. The method desirably further includes attaching a supplemental access device to the head of the pedicle fastener. According to this aspect of the invention, the supplemental access device desirably provides a second pathway extending from the incision to the head of the pedicle fastener.

According to another aspect of the invention, the step of removing at least a portion of the percutaneous access device may cause the cross-sectional area of the first pathway to be substantially reduced or eliminated. According to this aspect of the invention, a cross-sectional area of the second pathway transverse to a longitudinal axis of the supplemental access device preferably has substantially the same size as a cross-sectional area of the first pathway transverse to a longitudinal axis of the percutaneous access device.

According to another aspect of the invention, the percutaneous access device preferably includes first and second slots diametrically opposed to one another so that a fixation rod may pass through the slots along a direction transverse to a longitudinal axis of the percutaneous access device. According to yet another aspect of the invention, the supplemental access device preferably includes first and second slots diametrically opposed to one another so that a fixation rod may pass through the slots along a direction transverse to a longitudinal axis of the supplemental access device. According to yet a further aspect of the invention, the method preferably includes inserting the fixation rod into the body of the patient along at least a portion of the second pathway provided by the supplemental access device, such that the fixation rod passes through at least one of the slots of the supplemental access device.

According to another aspect of the invention, the percutaneous access device preferably includes a first and second blade spaced apart from one another and extending substantially parallel to one another when connected to the head of the pedicle fastener. According to this aspect of the invention, the first and second slots of the percutaneous access device are preferably defined by the first and second blades, the slots extending along the longitudinal axis of the percutaneous access device between the first and second blades.

According to another aspect of the invention, the first and second blades are preferably each integrally formed with the head of the pedicle fastener and connected thereto by a frangible portion.

According to another aspect of the invention, the step of removing at least a portion of the percutaneous access device may include removing the first blade from the head of the pedicle fastener. According to yet another aspect of the invention, the step of attaching the supplemental access device to the head of the pedicle fastener preferably includes receiving the second blade in a receiving structure of the supplemental access device.

According to another aspect of the invention, the step of removing at least a portion of the percutaneous access device may include removing both of the first and second blades from the head of the pedicle fastener. According to yet another aspect of the invention, the step of attaching the supplemental access device to the head of the pedicle fastener preferably includes engaging a gripping member and a locking member of the supplemental access device with the head of the pedicle fastener. According to this aspect of the invention, the locking member is preferably adapted to prevent disengagement between the gripping member and the head of the pedicle fastener.

Further aspects of the invention provide an access device for percutaneously accessing a pedicle fastener connected to a vertebra of a patient. The access device according to this aspect of the invention desirably includes an elongate gripping member and an elongate locking member. The elongate gripping member desirably has a body portion and also has first and second legs. Each of the legs desirably has a proximal portion connected to the body portion and a distal portion for engagement with a head of a pedicle fastener. The distal portion of each of the first and second legs desirably includes a first prong and a second prong. The first and second prongs desirably have a longitudinal slot between them which permits the first and second prongs to deflect relative to each other. The distal portions of the first and second legs are desirably deflectable away from one another so as to engage and disengage the head of the pedicle fastener. According to this aspect of the invention, the elongate member is connected to and movable relative to the gripping member between a retracted position and a locked position. The locking member preferably prevents the first and second legs of the gripping member from deflecting away from one another when the locking member is in the locked position.

According to another aspect of the invention, the locking member preferably includes at least one projection arranged to be received within the slot between the first and second prongs of either the first or second legs of the gripping member. According to this aspect of the invention, movement of the locking member to the retracted position preferably causes the projection to move within the slot so as to deflect the first and second prongs away from one another.

According to another aspect of the invention, the locking member preferably includes at least one projection arranged to be received within a recess in the gripping member. According to this aspect of the invention, movement of the locking member to the locked position preferably causes the projection of the locking member to move into the recess of the gripping member so as to restrain movement of the first and second prongs away from one another.

According to another aspect of the invention, the gripping member is preferably received within the locking member. The locking member preferably has a generally curved interior surface shaped to substantially match an exterior surface of the gripping member. The locking member also preferably includes a substantially flat exterior surface.

Yet further aspects of the invention provide an access device for percutaneously accessing a fixed pedicle fastener, which pedicle fastener preferably has a head and a blade. The access device according to this aspect of the invention desirably includes an elongate tubular body defining a central bore therethrough and a groove spaced from the central bore. The groove is desirably dimensioned to receive the blade therethrough. A distal end of the tubular body is desirably adapted for engagement with the head of the fastener.

Yet further aspects of the invention provide a retractor for inserting or positioning a fixation rod in a pedicle fastener. The pedicle fastener preferably has a head and a blade extending therefrom. The blade preferably has a plurality of holes in linear alignment along its proximal portion, and the head preferably has a groove therein. The retractor according to this aspect of the invention desirably includes a body, a first leg extending from the body, and a second leg extending from the body. The body desirably defines a central bore having a longitudinal axis therethrough. The body desirably has grooves for gripping around a circumference thereof. The body desirably has at least one deflectable arm formed through a thickness of the body. The deflectable arm is desirably a partial cutout of the thickness of the body such that the arm is predisposed to bending in a lateral direction. The arm desirably has an inwardly extending boss. The first leg desirably has a first prong on its distal end for insertion into the groove of the head of the pedicle fastener. The first leg desirably has a plurality of holes in linear alignment along its distal portion. The second leg desirably has a second prong on its distal end for insertion into the groove of the head of the pedicle fastener. According to an aspect of the invention, the body preferably includes a groove therein offset from an inner perimeter of the central bore. The groove is desirably dimensioned to receive the blade of the pedicle fastener such that the blade is not removable from the groove in a lateral direction. The groove desirably shares inner edges with the central bore.

Yet further aspects of the invention provide a system for inserting or positioning a fixation rod in a pedicle fastener. The pedicle fastener preferably has a head and a blade extending therefrom. The blade preferably has a plurality of holes in linear alignment along its proximal portion, and the head preferably has a groove therein. The system according to this aspect of the invention desirably includes a persuader and also desirably includes a retractor in accordance with aspects of the invention described above. The persuader desirably includes a body having an inner perimeter approximately equal to an outer perimeter of the retractor such that the persuader is slidable along the length of the retractor. The body of the persuader desirably has a viewing window for viewing the relative positions of the retractor and the persuader during placement of the persuader. The inner perimeter of the persuader is desirably dimensioned to confine the retractor when the blade of the fastener is received in the retractor. The body of the persuader desirably includes one of a plurality of protrusions and a plurality of holes in linear alignment for engagement with a plurality of holes along a distal portion of the first leg of the retractor. A distal surface of the body of the persuader is desirably adapted for exerting a force against the fixation rod to cause the fixation rod to move in a distal direction. The persuader desirably also includes a hollow flange. The hollow flange preferably extends at an oblique angle to a longitudinal axis of the body. The persuader desirably also includes a handle assembly. The handle assembly preferably extends at an oblique angle to the longitudinal axis of the body. The handle assembly desirably has a connecting rod attached to the hollow flange by a fastener, and the connecting rod desirably has a handle extending therefrom.

Yet further aspects of the invention provide a method for inserting or positioning a fixation rod in a pedicle fastener. The pedicle fastener preferably has a head and a blade extending therefrom. The blade preferably has a plurality of holes in linear alignment along its proximal portion, and the head preferably has a groove therein. The method according to this aspect of the invention desirably includes placing a retractor in accordance with aspects of the invention described above over the blade of the fastener. The method desirably further includes sliding the retractor such that the first and second prongs of the retractor are inserted into the groove of the head of the pedicle fastener. The method desirably further includes placing a persuader in accordance with aspects of the invention described above over at least the first and second prongs of the retractor. The method desirably further includes sliding the persuader along the length of the retractor to exert a force against the fixation rod to cause the fixation rod to move in a distal direction.

Yet further aspects of the invention provide a coupling for receiving and maintaining positioning of adjacent blades of a pedicle fastener. The blades preferably have at least one hole. The coupling according to this aspect of the invention desirably includes a tubular body having a thickness and defining a central bore therethrough. The tubular body desirably includes at least two spaced apart channels therein. Each channel is desirably dimensioned to receive an adjacent blade therethrough. The tubular body desirably includes at least one tab formed through the thickness. The tab is desirably deflectable into the central bore for engagement with at least one of the holes of the adjacent blades.

Yet further aspects of the invention provide a coupling for receiving and maintaining positioning of adjacent blades of a pedicle fastener. The coupling according to this aspect of the invention desirably has inner and outer perimeters spaced apart by a thickness and extending along a length from a proximal to a distal end thereof. The inner perimeter desirably defines a central hole having a longitudinal axis centrally located therethrough. The coupling desirably defines a gap extending through its thickness and along its entire length. The coupling desirably further includes a pair of opposing channels extending along the longitudinal axis. Each of the channels is desirably defined by opposing protrusions on both the proximal and distal ends of the coupling. Each of the channels desirably extends from the inner perimeter into the thickness, and each of the channels is desirably dimensioned to receive one of the adjacent blades of the pedicle fastener such that the blade is not removable from the corresponding channel in a lateral direction. The coupling desirably further includes opposing deflectable tabs formed in the thickness and located within corresponding opposing slots, such that the tabs are predisposed to bending in the lateral direction. Each of the tabs desirably has an inwardly extending protuberance. The coupling desirably further includes a recess extending from the proximal end through the thickness. The recess is desirably dimensioned to receive a fixation rod. The recess is desirably located opposite the gap in the coupling. The coupling desirably further includes flanges at both the proximal and distal ends. The flanges desirably have a wider thickness than a portion of the coupling between the flanges.

Yet further aspects of the invention provide a coupling system for receiving and maintaining positioning of adjacent blades of adjacent pedicle fasteners. The coupling system according to this aspect of the invention desirably includes a pair of couplings in accordance with aspects of the invention described above. Each of the couplings is desirably placed on the adjacent blades of one of the adjacent pedicle fasteners. The coupling system desirably further includes a fixation rod placed within each of the recesses of the pair of couplings.

BRIEF DESCRIPTION OF THE DRAWINGS

FIGS. 1A and 1B show perspective views of a spinal fixation system during and after insertion of a fixation rod thereof, respectively, as known in the prior art.

FIG. 5 shows a perspective view of a blade rescue retractor of the blade rescue system of FIG. 4 being placed over the blade-screw of FIG. 3.

FIGS. 6A and 6B show perspective and cross-sectional elevation views of the retractor of the blade rescue system of FIG. 4 assembled to the blade-screw of the blade rescue system of FIG. 4.

FIG. 7 shows a perspective view of a persuader of the blade rescue system of FIG. 4 placed over the blade-screw of FIG. 3.

DETAILED DESCRIPTION

Where reference is made herein to directional terms such as "proximal," "proximal most," "distal," and "distal most," it is to be understood that "proximal" and "proximal most" refer to locations closer to a user or operator of the device or method being described and that "distal" and "distal most" refer to locations further from a user or operator of the device or method being described.

Figure 1B:
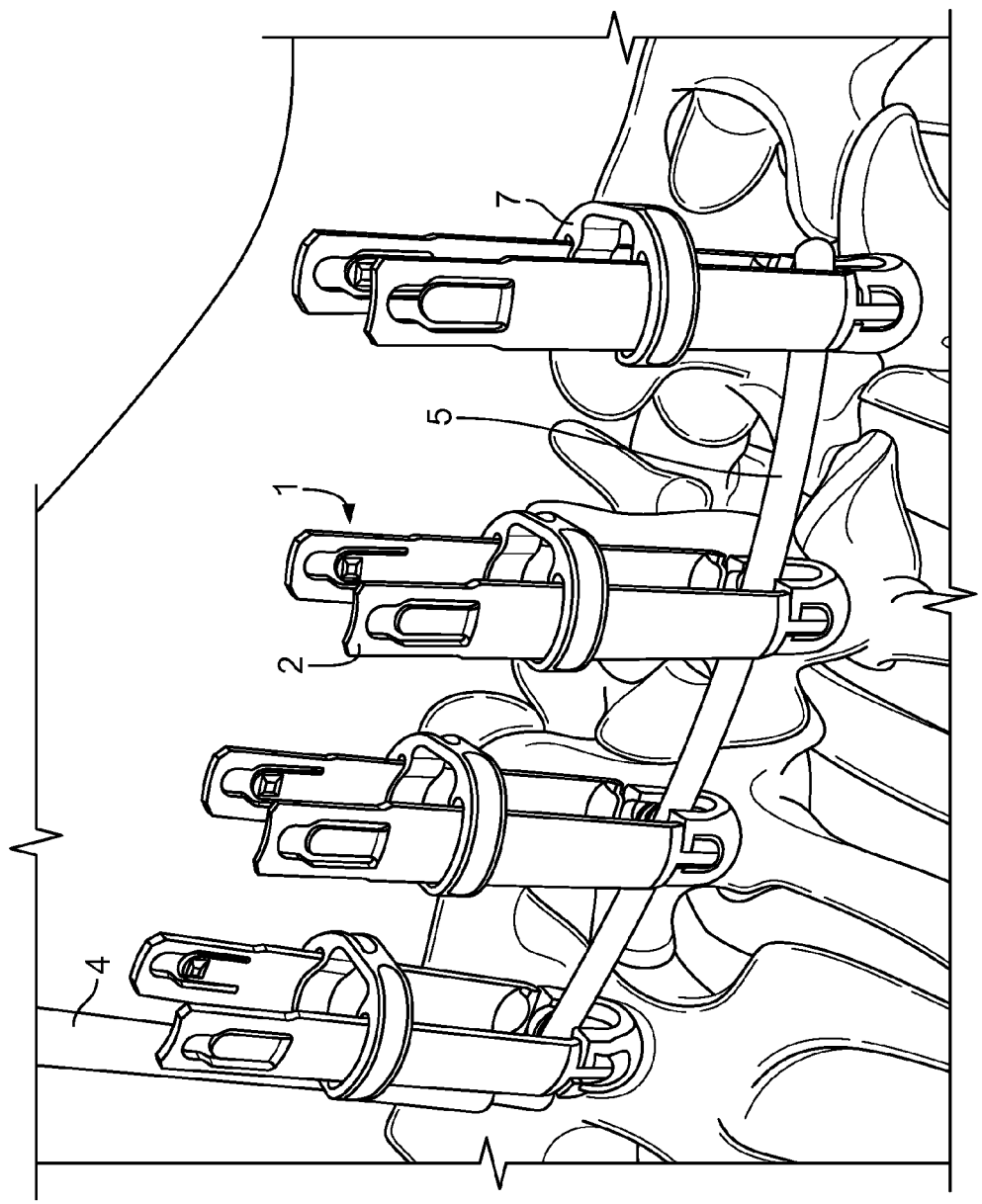
Figure 2B:
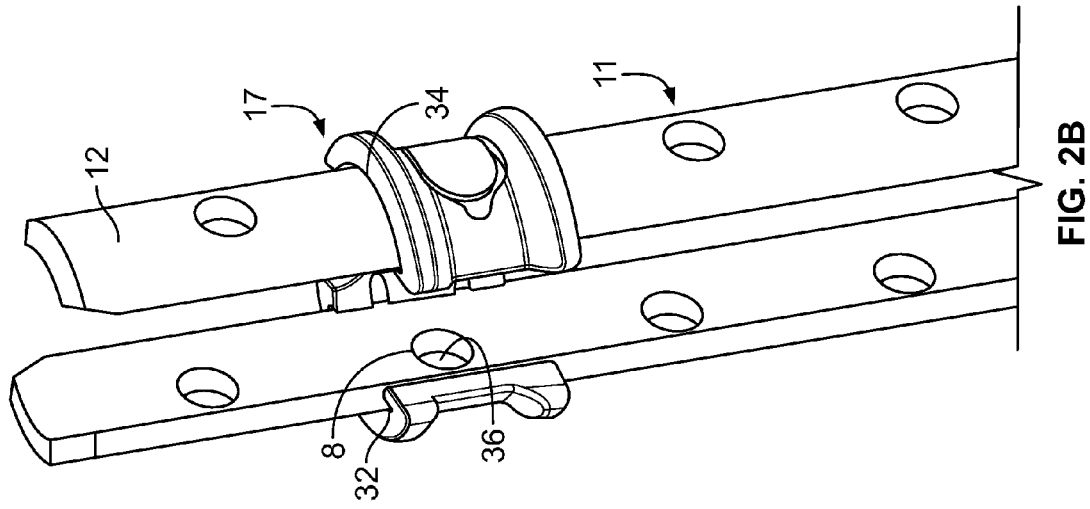
FIG. 2B shows a perspective view of an assembly of a pedicle blade-screw and a coupling in accordance with an embodiment of the present invention.
Figure 2A:
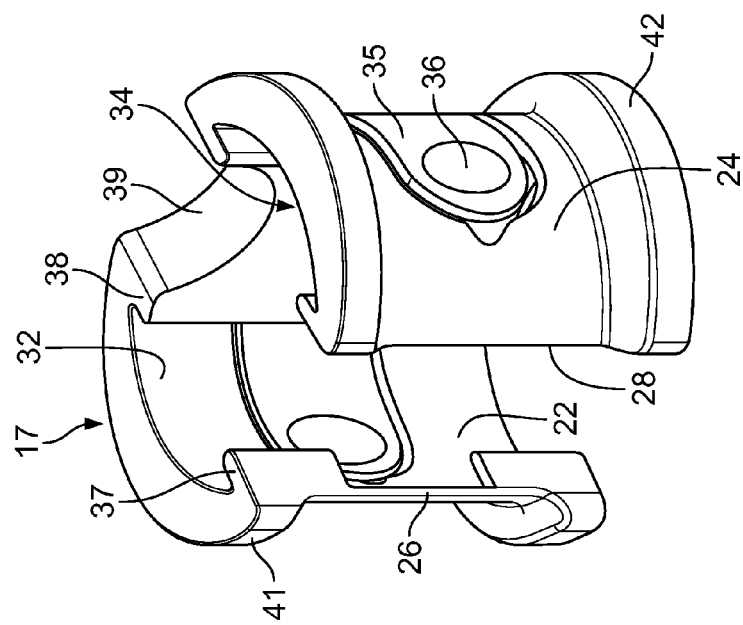
FIG. 2A shows a perspective view of an arrangement of a coupling in accordance with an embodiment of the present invention.

Referring to FIGS. 2A and 2B, in accordance with one embodiment, a coupling 17 may include inner and outer perimeters 22, 24 spaced from one another by a thickness of the coupling 17 in which the inner perimeter 22 defines a central opening along a longitudinal axis of the coupling 17. As shown, the coupling 17 may have ends 26, 28 spaced from one another such that the ends 26, 28 define a gap passing through the inner and outer perimeters 22, 24 and the thickness therebetween. As shown, the coupling 17 may be in the form of a "c-ring," although other shapes, such as but not limited to a square having a gap through one of the sides, may be used.

The coupling 17 may be placed over and assembled with an integrally formed blade-screw 11, as shown in FIG. 2B, or in some arrangements, a blade-screw that may be an assembly of a blade and a pedicle screw attached by a fastener, through a snapped connection, or by other attachment mechanisms known to those of ordinary skill in the art. To attach the coupling 17 to the blade-screw 11, the coupling 17 may include opposing channels 32, 34 set in or offset from the inner perimeter 22 that may receive the opposing blades 12 therethrough, as shown in FIGS. 2A and 2B. In this manner, the coupling 17 may maintain separation between the opposing blades 12 to stabilize and provide stiffness to the blades 12 during one or both of insertion of the blade screw 1 into the body and insertion of the fixation rod 5 into the blade-screw 1, and to provide the surgeon or other qualified user with direct visualization of the fixation rod 5 during insertion thereof. Moreover, the opposing channels 32, 34 may be dimensioned to align and orient the blades 12 of the blade-screw 11 at a particular angular position relative to each other.

As shown, in some arrangements, each of the channels 32, 34 may be defined by protrusions 37, 38 that may form spaced apart walls separating the inner perimeter 22 from the channels 32, 34. In this manner, such walls may have edges common to both the inner perimeter 22 and the respective opposing channels 32, 34. Such protrusions 37, 38 desirably secure the blades 12 within the channels 32, 34 by preventing the blades 12 from moving inwardly towards each other. In some arrangements, to secure one of the blades in a channel, at least one protrusion may be located at the proximal end and at least one protrusion may be located at a distal end on one side of the coupling.

As shown, in some arrangements, the coupling 17 may include either or both of upper and lower flanges 41, 42 that may extend outwardly away from the longitudinal axis of the coupling 17 to stiffen the coupling 17 and also to provide surfaces against which a user may push to ease the sliding of the coupling 17 along the blades 12. A flexible tab 35, which may include a boss or protuberance 36 extending inwardly from the inner perimeter 24 towards the longitudinal axis may extend around a portion of the coupling 17. As shown, the tab 35 may be formed by making a U-shaped cut through the thickness of the coupling 17 between the inner and outer perimeters 22, 24. As illustrated in FIG. 2B, the blades 12 may include one or more holes 8 along a length of the blades 12 which pass through a thickness of the blades 12 and which may be sized to receive the boss 36 of the flexible tab 35 of the coupling 17. In some arrangements, the coupling 17 may be flexible such that the ends 26, 28 are separated a greater distance when the coupling 17 is placed over the opposing blades 12 than when the coupling 17 is not in use. In this manner, when the coupling 17 is placed over the opposing blades 12, each of the tabs 35 may be predisposed to compress against the respective blades 12 such that the respective bosses 36 of the tabs 35 protrude slightly into the holes 8 as the bosses 36 passes over the holes 8. In this manner, the coupling 17 provides feedback to the user that the coupling 17 is in a predetermined location.

In some arrangements, at least a pair, and desirably all, of couplings 17 forming a set of couplings may each include a recess 39, in which each such recess 39 may be located opposite the respective gaps defined by the ends 26 and 28 of the respective couplings 17. In such arrangements, each of the holes 8 of the opposing blades 12 engaged by each of the set of couplings 17 may be located at the same relative heights along the respective blades 12. In this manner, when each blade-screw 11 of a set of blade-screws are inserted to a predetermined position in the vertebrae of a patient and the tabs 35 of the set of couplings 17 are placed such that the bosses 36 of the tabs 35 are aligned to protrude into the holes 8 at the same relative positions along the blades 12 of the respective blade-screws 11, the recesses 39 of the couplings 17 will be spaced above the respective pedicle screw heads (not shown) of the blade-screws 11 by the same height. Therefore, the relative positioning of the recesses 39 will desirably mimic the relative positioning of the rod receiving surfaces 55 (see FIG. 3 for example) in the pedicle screw heads of the blade-screws 11 into which the fixation rod 5 is to be placed. The distances between the recesses 39 may thus be used to help determine an appropriate length for the fixation rod 5. Additionally, the recesses 39 provide an extracorporeal template for contouring or selecting a fixation rod 5 to be implanted in the same manner as the rod configuration systems disclosed in commonly owned U.S. Pat. No. 8,177,817 ("the '817 patent") and U.S. Patent Application Publication No. 2007/0233079 ("the '079 Publication"), the entireties of which are hereby incorporated by reference herein as if fully set forth herein. For example, the recesses 39 are desirably shaped to receive and support an appropriately shaped fixation rod 5 in a position such that the fixation rod 5 simultaneously extends through the various recesses 39. The fixation rod 5 may thus be contoured (e.g., with a French bender), selected from a kit of pre-shaped rods, or custom fabricated (e.g, by a CNC procedure) such that the rod 5 provides an optimal fit within the recesses 39, and thus, in turn, within the rod receiving surfaces 55 of the pedicle screw heads of the blade-screws 11. In another arrangement, one or more bridges (not shown), as described in the '817 patent and the '079 Publication, may be used to couple together two or more of the blade-screws 11 and constrain their relative orientations (e.g., such that they are substantially parallel to one another).

Figure 3:
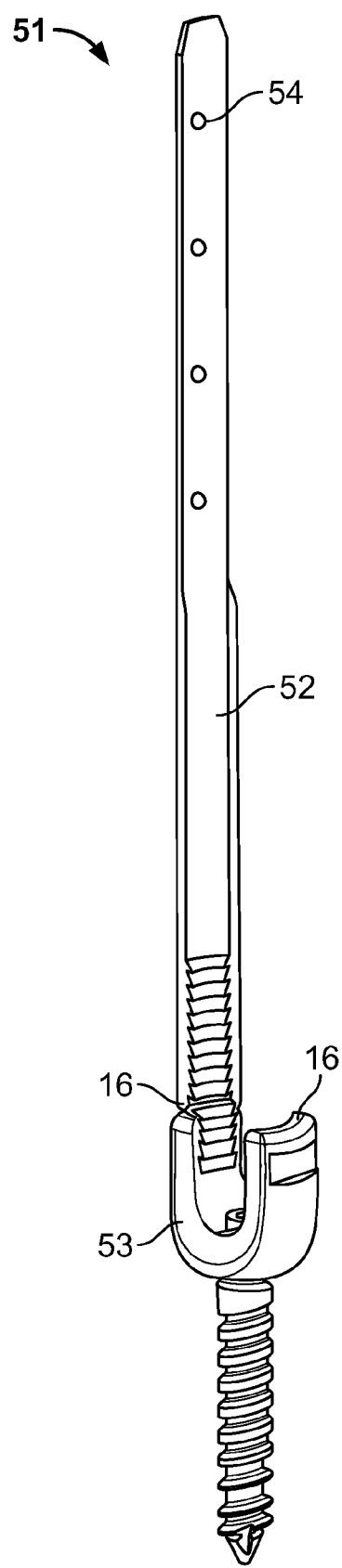
FIG. 3 shows a perspective view of a pedicle blade-screw having a single blade.

Referring now to FIG. 3, a blade-screw 51 may include only a single blade 52 extending from a pedicle screw head 53 in contrast to the blade-screws 1, 11 previously described herein, which may be due to a previously attached opposing blade having become disconnected from the pedicle screw head 53. For example, the previously attached opposing blade may have been unintentionally broken off at the frangible portion 16, or the blade may have been intentionally broken off before it was determined that further revision may be necessary. In such a configuration, the blade-screw 51 may be unable to provide a percutaneous pathway for the insertion of a fixation rod such as the rod insertion tool 4 previously described herein.

Figure 4:
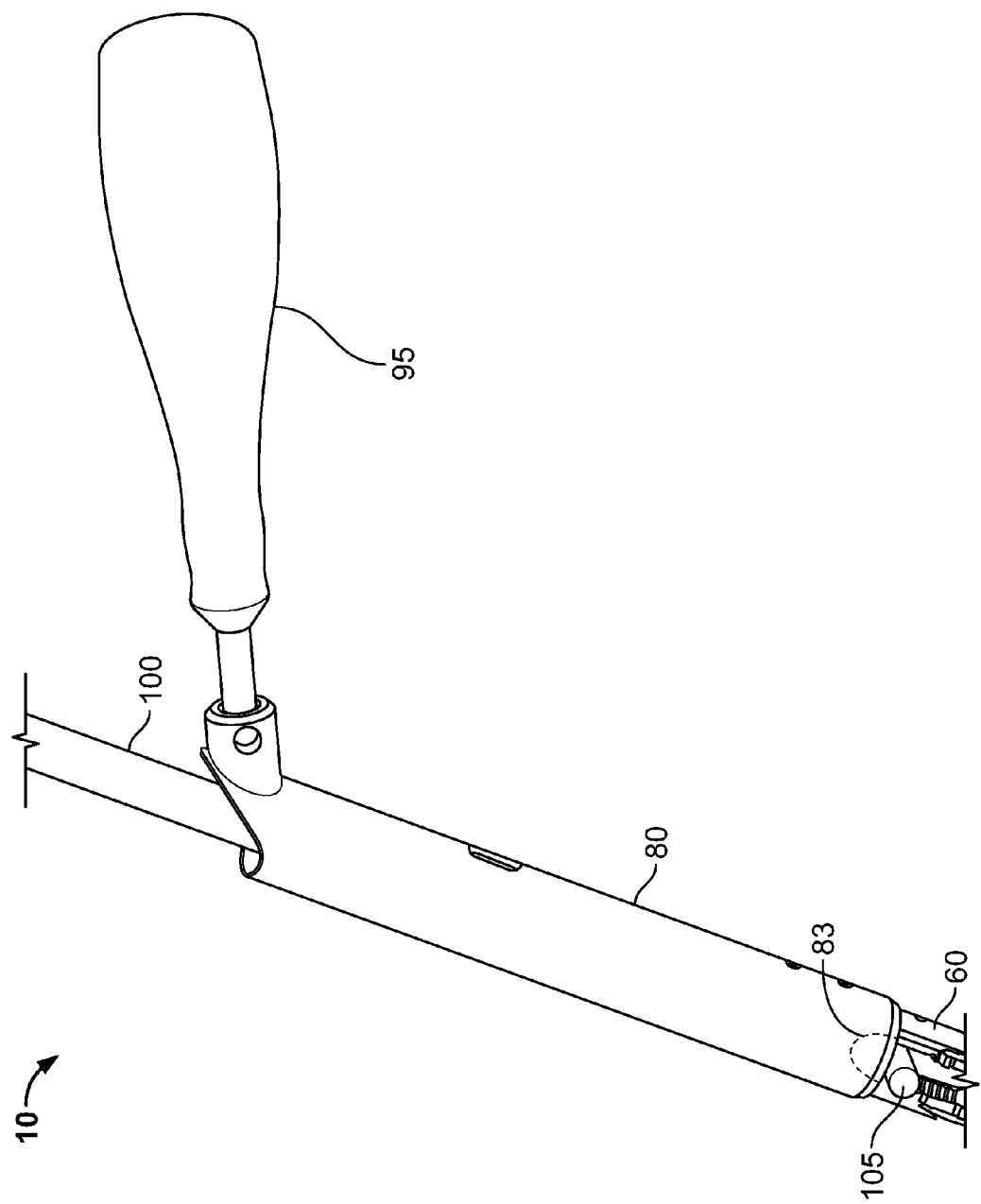
FIG. 4 shows a perspective view of a blade rescue system including the pedicle blade-screw of FIG. 3 in accordance with an embodiment of the present invention.

As shown in FIG. 4, a blade rescue system 10 may be utilized to insert a fixation rod 105 by using the single blade 52 of the blade-screw 51. Along with the blade-screw 51, the blade rescue system 10 may include a blade rescue retractor 60 that may be placed over and engaged with a blade-screw 51. A persuader 80 having a handle 95 extending therefrom described further herein may be placed over and engaged with the retractor 60. In this configuration, a blocker inserter assembly 100 may be inserted along a central longitudinal axis within the assembly of the blade-screw 51, the retractor 60, and the persuader 80, into engagement with the blade-screw 51 in order to guide and persuade the insertion of the fixation rod 105.

As illustrated in FIGS. 5, 6A, and 6B, the retractor 60 may include a body 65 having opposing first and second legs 64, 66 extending in a distal direction therefrom. The retractor 60 may have a generally tubular shape, and the legs 64, 66 may define diametrically opposed slots 67 extending proximally from the distal end of the retractor 60. Such slots 67 desirably provide a space through which a fixation rod may pass, and, in some instances, provide a viewing window between the legs 64, 66. The retractor 60 may be placed over the blade-screw 51 such that the blade-screw 51 is received within an inner perimeter 77 of the retractor 60. To facilitate such placement, a gripping aid 61, such as parallel grooves at a proximal portion of and perpendicular to the central axis of the retractor 60, knurling (not shown), or other friction-inducing features may be added to the retractor 60. As shown, in some arrangements, the inner perimeter 77 of the retractor 60 may include an inner diameter 78 defining a central bore having a longitudinal axis which may receive the blocker inserter assembly 100. In some arrangements, a groove 79 may be offset from the inner diameter 78 along a length thereof. In this manner, the retractor 60 may be placed over the blade-screw 51 such that the single blade 52 of the blade-screw 51 may slide within and along a length of the groove 79. In some arrangements, the groove 79 may have a shape similar to the grooves 32, 34 of the coupling 17 as described above. Furthermore, in some arrangements, the groove 79 may interface with the inner perimeter 77 in a manner similar to the interfaces of the grooves 32, 34 and the inner perimeter 22 of the coupling 17 (e.g., having protrusions to secure the blade 52 within the groove).

As best shown in FIG. 6B, the first leg 64 may extend over the blade 52. As further shown, in some arrangements, the first leg 64 may have a thickness such that a total thickness of the first leg 64 and the blade 52 is approximately, i.e., within at least 10% and more preferably, within 1%, and still more preferably within 0.1%, of the thickness of the second leg 66. In this manner, the first leg 64 of the retractor 60 may provide sufficient, and, in some arrangements, balanced rigidity to prohibit bending of the first leg 64 during insertion of a fixation rod while extending only minimally beyond the outer width dimension of the blade-screw 51, consistent with the desire that the pathway through the tissue be as minimally invasive as possible.

Referring again to FIG. 5 as well as to FIGS. 6A and 6B, the retractor 60 may include an arm 62 extending from the body 65 thereof. As shown, the arm 62 may extend from or be formed by a cutout of the body 65. As further shown, a boss 63 may extend inwardly from the inner diameter 77 of the retractor 60. In this manner, when the retractor 60 is placed over the blade 52 of the blade-screw 51, the boss 63, or in some arrangements, a plurality of bosses, may be predisposed to extend into one or more recesses or holes 54 of the blade 52. The holes 54 may have a nominal diameter of 2 mm, although the holes 54 may have a different diameter. In some arrangements, the boss 63 may have a diameter slightly less than the diameter of the holes 54, while in other arrangements, the boss 63 may have a diameter slightly greater than the diameter of the holes 63 such that an interference fit may be established upon insertion of the boss 63 into one of the holes 54. In configurations having a plurality of holes 54, such holes may be placed in linear alignment along a length of the blade 52 such that the retractor 60 may be maintained at various positions relative to the blade-screw 51. As shown, in some arrangements, the corresponding hole or holes 54 of the blade-screw 51 may be placed near a proximal end of the retractor 60.

As best shown in FIG. 6B, in some arrangements, the first and second legs 64, 66 of the retractor 60 may include respective prongs 68, 69 at the distal end of the retractor 60. The pedicle screw head 53 of the blade-screw 51 may include a corresponding groove 56 around at least a portion of the perimeter thereof for receiving the prongs 68, 69. As further shown, in some arrangements, the first and second legs 64, 66 of the retractor 60 may include grooves 71, 72. In such arrangements, the head 53 of the blade-screw 51 may include a protrusion 57 around at least a portion of the perimeter thereof that may be inserted into the grooves 71, 72 of the retractor 60. In this manner, the retractor 60 may be placed into locking engagement with the blade-screw 51.

Figures 8A, 8B:
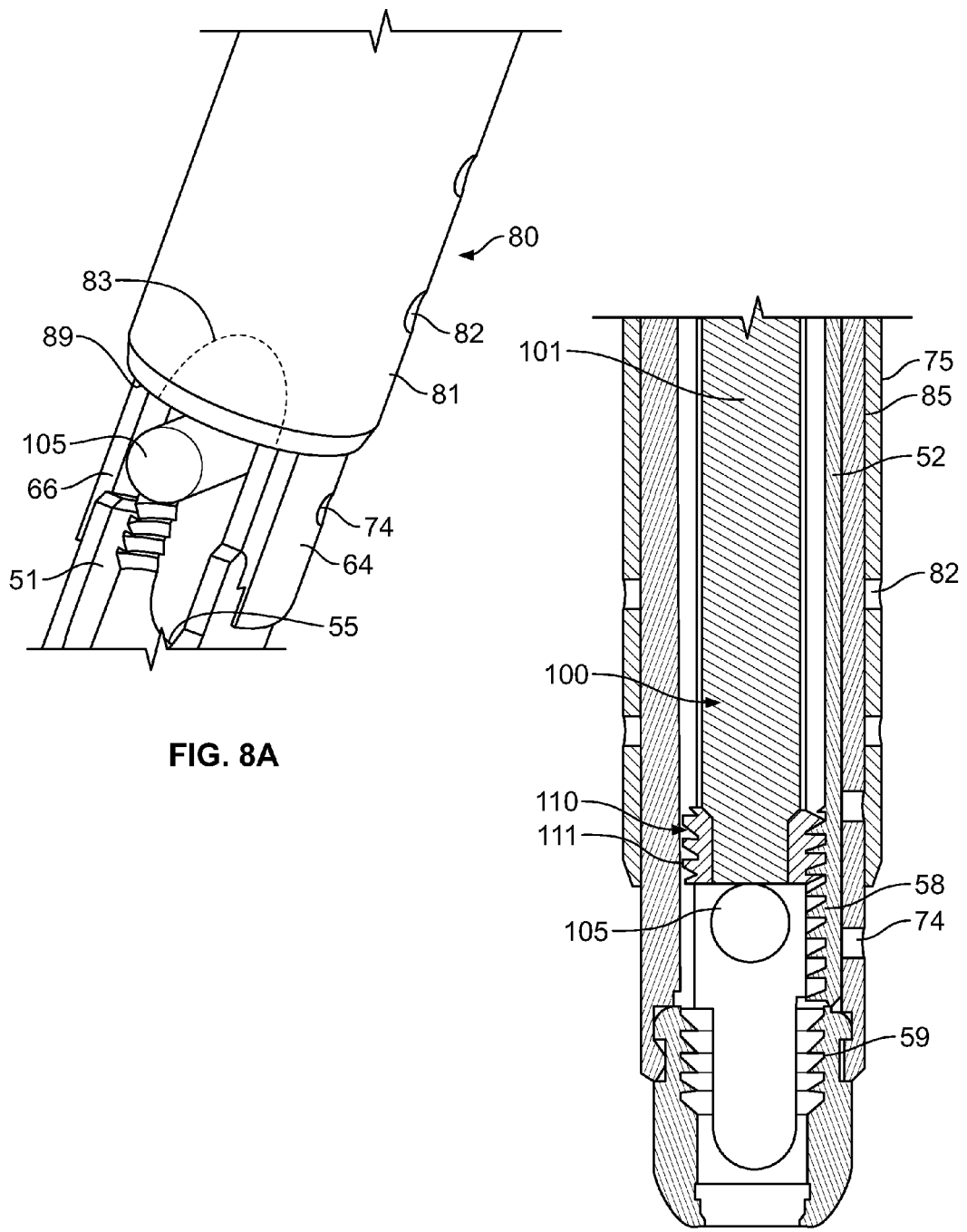
FIGS. 8A and 8B show enlarged perspective and cross-sectional elevation views of a distal portion of the blade rescue system of FIG. 4.

Now referring to FIG. 7 as well as FIGS. 8A and 8B, the persuader 80 may be placed over and into engagement with the retractor 60. As best shown in FIG. 8B, the persuader 80 may include a body 81 having an inner perimeter 85 along a length thereof that circumscribes a corresponding length of an outer perimeter 75 of the retractor 60. As shown, in some arrangements, the inner perimeter 85 of the persuader 80 and the outer perimeter 75 of the retractor 60 may have corresponding diameters in which the inner perimeter 85 is only slightly larger than the outer perimeter 75 such that the persuader 80 may slide over the retractor 60 with the least amount of angulation or play allowable without forming an interference fit with the retractor 60 that prevents removal of the persuader 80 from the retractor 60. The body 81 of the persuader 80 may include a viewing window 84, or, in some arrangements, a plurality of viewing windows, defining a hole or a plurality of holes through a thickness of the body 81. The window 84 may provide an area through which to view the relative positions of the retractor 60 and the persuader 80 during placement of the persuader 80, for example to determine whether the fixation rod 5 has been fully persuaded.

In some arrangements, the body 81 may include a flange 86, which may be hollow as shown in FIG. 7, extending at an oblique angle to a longitudinal axis defined by the inner perimeter 85 of the body 81. In some arrangements as further shown in FIG. 7, a handle assembly 95 may extend at an oblique angle to a longitudinal axis defined by the inner perimeter 85. The handle assembly 95 may include a handle 96, which may include a friction-inducing grip for reducing slipping that may otherwise be experienced by a user, that may extend from a connecting rod 97. As shown, the connecting rod 97 may be attached to the flange 86 by a fastener, which may be inserted through a fastener inner perimeter 87 defining a hole through the flange 86. In other arrangements, a connecting rod of a handle assembly may form an interference fit with a receiving bore of a hollow flange extending from the body into which the connecting rod may be inserted (not shown). In still other arrangements, a connecting rod of a handle assembly may form a monolithic structure with a flange extending from the body.

With the persuader 80 placed over the retractor 60, the blocker inserter assembly 100 may be inserted along a longitudinal axis of a space defined by the single blade 52 of the blade-screw 51 and the retractor 60. The blocker inserter assembly 100 may include a blocker inserter 101 that may be temporarily engaged with a blocker 110, in which such engagement may be through an interference fit between the blocker inserter 101 and the blocker 110. The blocker 110 may include external threads 111 that may engage corresponding threads 58 along a distal portion of the blade 52 and also threads 59 within the rod receiving surface 55 in the head 53 of the blade-screw 51. The blocker 110 may be rotated clockwise or counterclockwise by rotation of the blocker inserter 101 in a corresponding clockwise or counterclockwise direction to cause the blocker 110 to move distally or proximally, respectively.

The fixation rod 105 may be inserted within a working region defined by the blade 52 of the blade-screw 51 and the second leg 66 of the retractor 60 and the receiving surface 55 of the head 53 of the blade-screw 51, which may be in the shape of a saddle (as best shown in FIG. 6B), facing inwardly in a proximal direction, in which the receiving surface 55 may be U-shaped and the head 53 may be tulip-shaped as best shown in FIG. 3. In this configuration, the blocker 110 may contact the fixation rod 105 to push or persuade the fixation rod 105 distally towards the rod receiving surface 55 when the blocker 110 is turned in one direction and to allow the fixation rod to be raised proximally when the blocker 110 is turned in the opposite direction. During the insertion of the blocker 110, in some arrangements, the persuader 80 may confine the retractor 60 attached to the single blade 52 to prevent the retractor legs 64, 66 from splitting apart, i.e., separating in a direction away from each other. In this manner, the persuader 80 may prevent the retractor 60 from disengaging the blade-screw 51 during either of insertion of the blocker 110 into the working region described above or persuasion of the fixation rod 105. In some arrangements, the persuader 80 may have a distal surface to exert a force against the fixation rod 105 to cause the fixation rod 105 to move distally. In still further arrangements, the persuader body 81 optionally may have diametrically opposed recesses 83, as shown by the dashed lines in FIGS. 4 and 8A, at the distal end thereof for receiving the rod 5 therein in a transverse orientation. In some such arrangements, the fixation rod 105 may be pushed distally by the persuader 80 to a position such that the threads 111 of the blocker 110 may be engaged with either of the threads 58, 59 without contacting, and thus without interference caused by a proximal force due to, the fixation rod 105.

The persuader 80 may include one or more persuader holes 82 on a distal end of the persuader 80. When inserting the persuader 80 over the retractor 60, the body 81 of the persuader 80 may be positioned such that the persuader holes 82 and the holes 74 of the retractor 60 may be in alignment. In this manner, the persuader 80 may be placed in a position relative to the retractor 60 in which the holes 82 of the persuader 80 and the holes 74 of the retractor are placed in visual alignment. In some arrangements, this position may be located at a position at which the persuader should not be pressed further along the retractor 60. In an alternative arrangement, the persuader may include protrusions in place of the holes 82 in which such protrusions may be dimensioned to be inserted into the holes 74 of the retractor 60 in order to establish a desired relative alignment and position between the persuader and the retractor.

Figure 9:
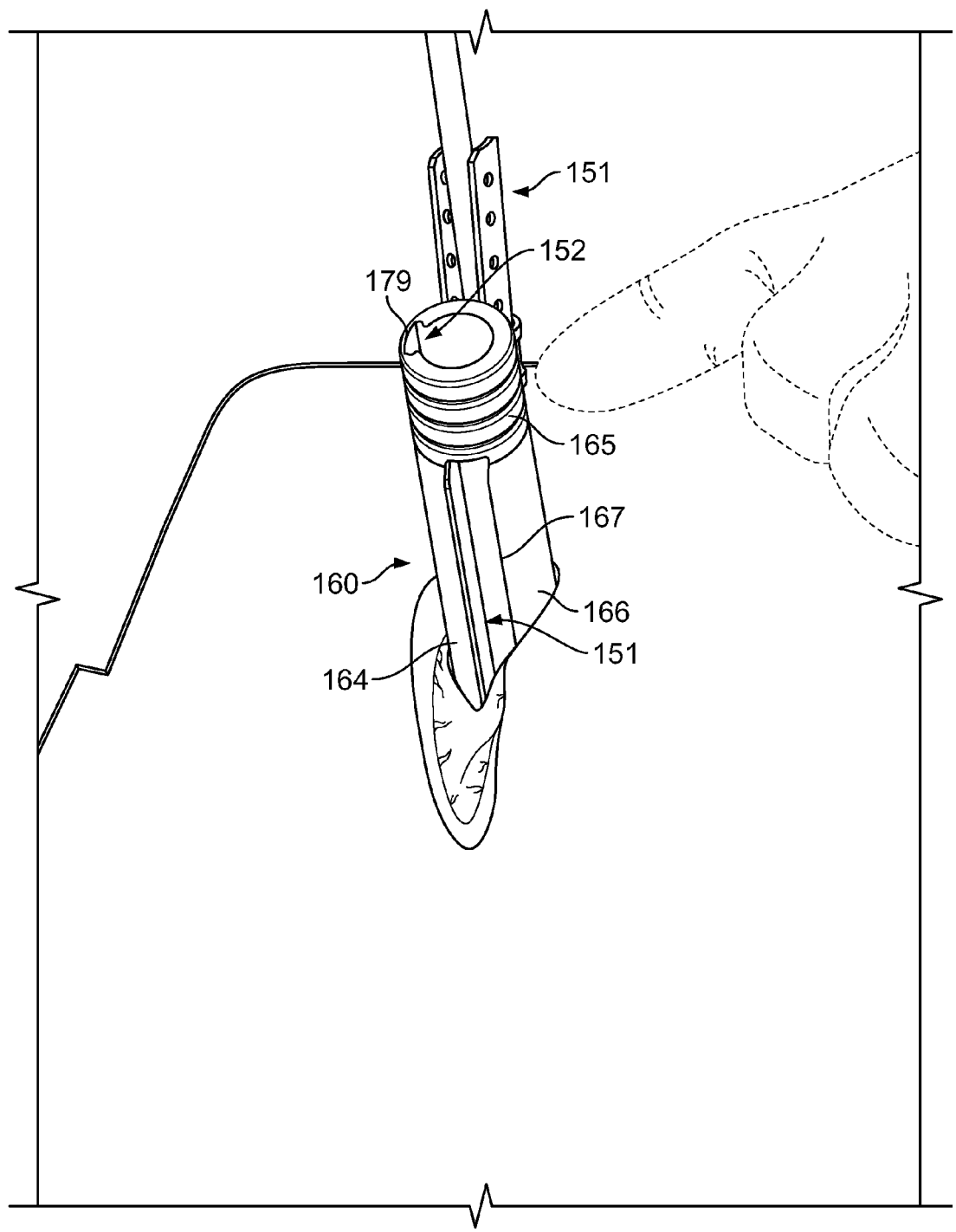
FIG. 9 illustrates the use of a blade rescue retractor over a blade-screw having a single blade during insertion of a spinal fixation rod during a spinal surgery in accordance with an embodiment of the present invention.
Figure 10:
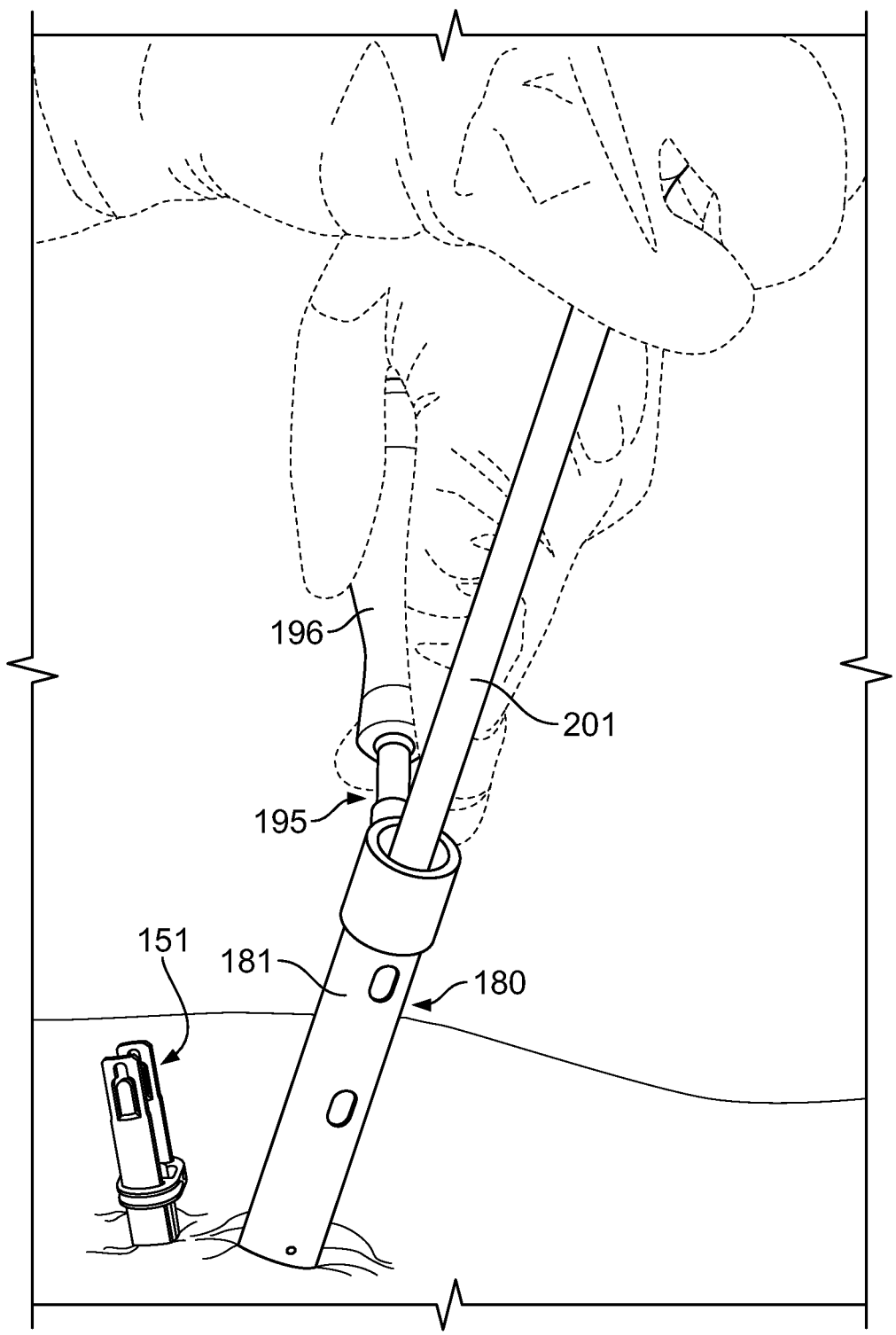
FIG. 10 illustrates persuasion of the spinal rod through the blade rescue system used during the spinal surgery illustrated in FIG. 9.

In operation as illustrated in FIGS. 9 and 10, in accordance with another embodiment, a qualified user, such as but not limited to a physician, a surgeon, a physician's assistant, and a veterinarian, may insert a pedicle blade-screw 151 into a pedicle of a spine. As shown, a blade of the blade-screw 151 may have been broken off or otherwise disconnected during insertion of the blade-screw 151 or during insertion of the fixation rod, while in rare instances, the blade-screw initially may have been produced with only a single blade. The user may place a retractor 160 over the pedicle blade-screw 151 such that the blade 152 of the blade-screw 151 may be inserted into a groove 179 of the retractor 160. The retractor 160 may have first and second legs 164, 166 extending from a body 165, the second leg 166 being on the same side as the groove 179, in which prongs extending from the legs 164, 166 may be separated a distance such that a first prong 168 and a second prong 169 (not shown) snap into a groove on a head of the blade-screw 151. (See FIG. 6B for example).

If the blade were to be disconnected before the fixation rod was inserted, the rod may be inserted using the retractor 160 as a functional replacement for the blade-screw 151 having a missing blade. That is, the second leg 166 opposite the remaining blade 152 desirably acts as a replacement for the missing blade by holding back the surrounding tissue, such that the retractor 160 provides a pathway through the tissue from the respective pedicle screw head to the incision through which the retractor 160 is disposed. Moreover, the slots 167 between the legs 164, 166 are analogous to the slots 67 between the blades of the blade-screws 51 described previously herein, as the slots 167 of the retractor 160 allow the rod 5 to extend transverse to the longitudinal axis of the retractor and be guided towards the pedicle screw heads.

After the fixation rod has been positioned within the body extending between one or more blade screws 151 and/or retractors 160, the rod may then be persuaded towards and into the rod receiving surfaces of the pedicle screw heads. Referring to FIG. 10, in some arrangements, a user may grab either or both of a body 181 or a handle 196 of a handle assembly 195, in which the handle 196 as shown may extend at an angle from the body 181, to place and position a persuader 180 over the retractor 160. The persuader 180 may then be advanced distally such that its distal end contacts the rod and persuades it towards the pedicle screw head, preferably at least until the rod is within the internally threaded region of the retractor blade 152 analogous to the threads on the blade 52 described previously herein. The persuader 180 desirably overlaps the first and second prongs 168, 169 of the retractor 160 to maintain the prongs 168, 169 within the groove on the head of the blade-screw 151. Once the rod is positioned within the internally threaded region of the retractor blade 152, the rod may be persuaded the remaining distance to the rod receiving surface of the pedicle screw head by using the blocker inserter 201 having a blocker (not shown) positioned on its distal end. Specifically, the blocker inserter 201 with blocker is inserted along the longitudinal axis of the retractor 160, as shown in FIG. 10. The external threads of the blocker are then engaged with the internal threads of the blade-screw 151, which may be on either or both of the blade 152 and the head of the blade-screw 151, and the blocker is advanced distally along the threads by rotating the blocker with the blocker inserter 201, thereby pushing the rod distally with the distal end of the blocker. In some arrangements, the user may push the persuader 180 against the fixation rod (see FIGS. 7 and 8A for example) to persuade the fixation rod to cause the fixation rod to move distally and to maintain separation between the fixation rod and the blocker during insertion of the blocker into the working region. In this manner, the persuader may reduce or remove a proximal, often undesirable, force that may otherwise be exerted by the fixation rod against the blocker due to contact between the rod and the blocker during insertion. Once the blocker is finally tightened within rod receiving surface of the pedicle screw head, thus capturing and securing the rod within the screw head, the blocker inserter 201 and persuader 180 may be removed from the body. Thereafter, the retractor 160 may be removed, in some arrangements by first applying an outward force on the arm (see FIGS. 6A and 6B for example) of the retractor 160 to disengage the boss of the arm from the recess (see FIGS. 3 and 6B for example) in the blade 152. Once the retractor 160 has been removed from the body, the remaining blade 152 may be broken off, such as by pivoting the blade 152 about the frangible portion (see FIG. 3 for example) until the frangible portion breaks. After all of the desired components have been removed from the body, the incisions through which the blade screws 151 and other components of the blade rescue system extended may then be closed.

Figures 11, 12:
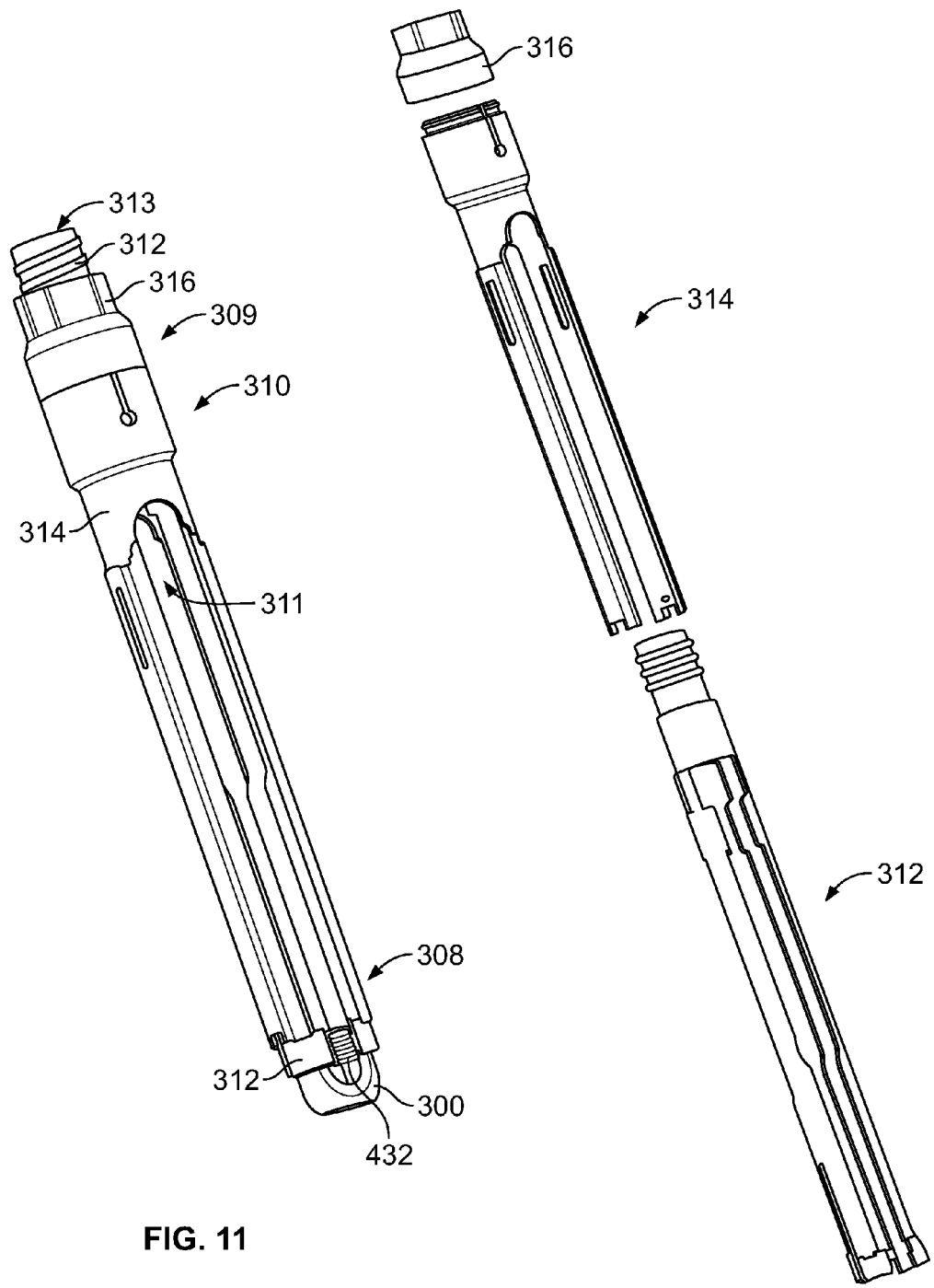
FIG. 11 illustrates a perspective view of a blade rescue retractor engaging a pedicle screw head in accordance with another embodiment of the present invention.
FIG. 12 illustrates a perspective, exploded view of the components of the blade rescue retractor of FIG. 11.

In accordance with another embodiment of a blade rescue system, a blade rescue retractor 310, as illustrated in FIG. 11, may be used when both blades have been disconnected from a pedicle screw head 300. The retractor 310 may define a longitudinal pathway 311 therealong between its distal end 308 and its proximal end 309. The retractor 310 may comprise a gripping member 312 and a locking member 314. In the embodiment of FIG. 11, both the gripping member 312 and the locking member 314 are hollow elongate bodies in which the gripping member 312 is received within the locking member 314. In operation, the locking member 314 may be constructed to move in a proximal direction and a distal direction along the gripping member 312. The retractor 310 desirably has an opening 313 into the longitudinal pathway 311 at its proximal end 309, which opening 313 may be defined by an opening at the proximal end of the gripping member 312. FIG. 12 is an exploded view of the retractor 310, illustrating the locking member 314 separated from the gripping member 312 and also illustrating the actuation mechanism 316 of the locking member 314 separated from the remainder of the locking member 314.

Figure 13:
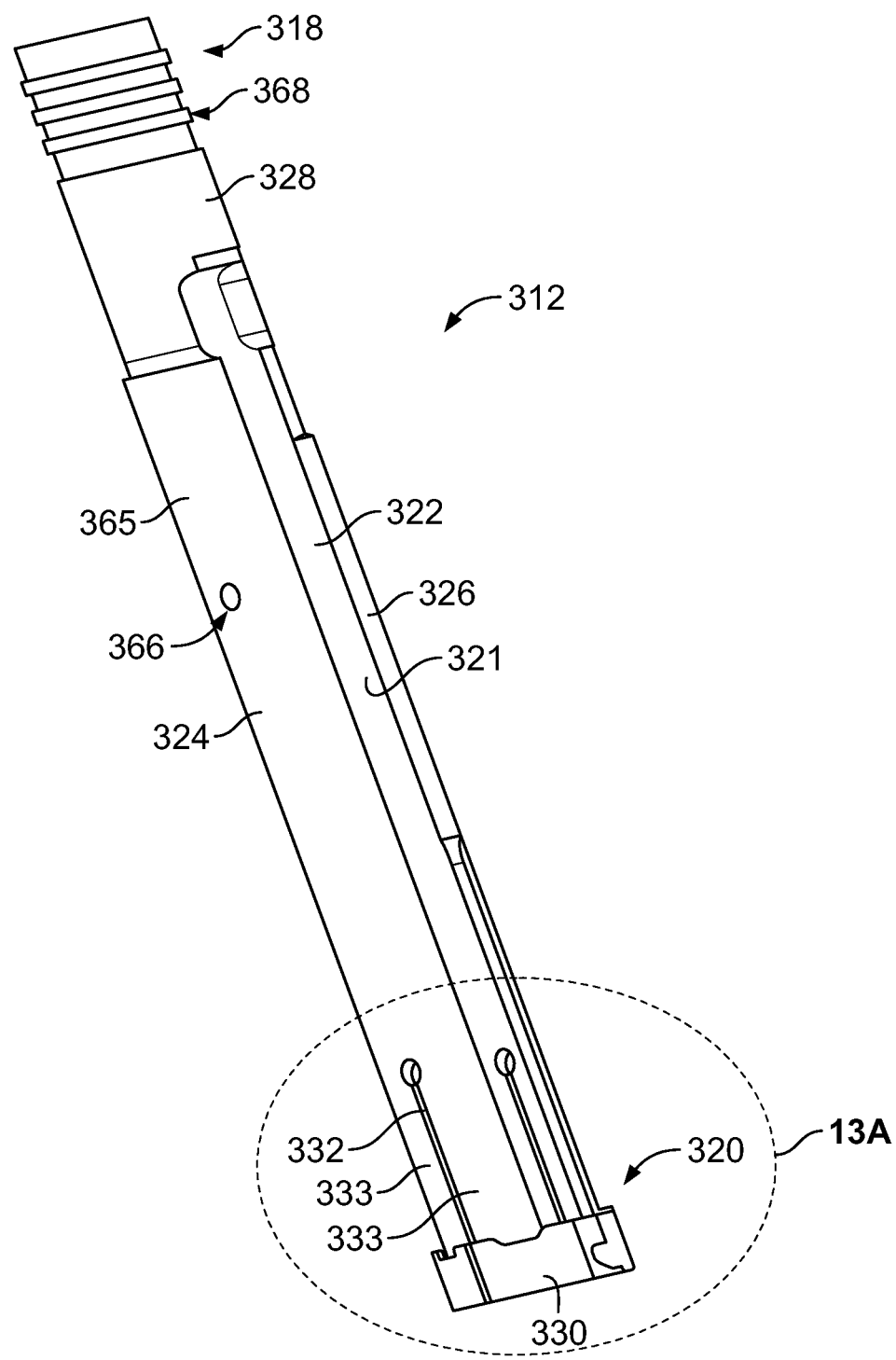
FIG. 13 illustrates a perspective view of a gripping member of the blade rescue retractor of FIG. 11.

The gripping member 312 is illustrated in FIG. 13, separated from the locking member 314 of the retractor 310. The gripping member 312 has a proximal end 318 and a distal end 320. An interior surface 321 of the gripping member 312 preferably defines the longitudinal pathway 311 along the retractor 310. In some embodiments, the interior surface 321 may include a threaded portion (not shown), preferably at least near the distal end 320 of the gripping member, for engagement with an externally threaded blocker and advancement of that blocker towards and into the pedicle screw head 300, as discussed above in connection with the embodiments illustrated in FIGS. 8B and 10.

Figure 13A:
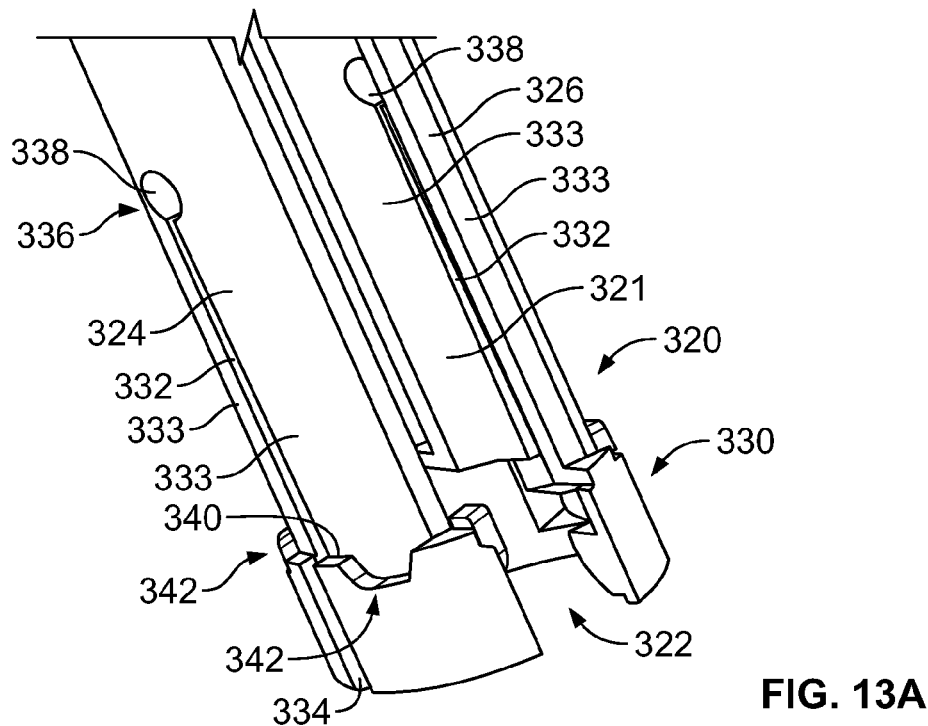
FIG. 13A illustrates an enlarged perspective view of section A in FIG. 13.

The gripping member 312 may have a generally tubular shape with diametrically opposed slots 322 extending proximally from the distal end 320 so as to define first and second legs 324, 326 extending distally from a body portion 328. Such slots 322 desirably provide a space through which a fixation rod may pass in an orientation transverse to the longitudinal axis of the retractor 310, and, in some instances, the slots 322 may provide a viewing window between the legs 324, 326. The gripping member 312 may be symmetrical on either side of the slots 322, such that the legs 324, 326 have the same structure. One or both legs 324, 326 of the gripping member 312 may include a slot 332 extending proximally from the distal end 320 so as to divide the distal portions of the legs 324, 326 into a plurality of prongs 333. As shown in FIG. 13A, which is a detail the slot 332 may have a distal end 334 open to the distal end 320 of the gripping member 312 and a proximal end 336 terminating at a hole 338. The hole 338 may be rounded to reduce stress concentrations at the proximal end 336 of the slot 332, and, in some embodiments, the hole 338 may be circular. The slot 332 is preferably tapered such that it narrows towards its proximal end 336. However, in other embodiments, the slot 332 may have a substantially constant width between its distal and proximal ends 334, 336. The gripping member 312 is desirably at least partially flexible, such that the legs 324, 326 can deflect at least slightly away from one another. The gripping member 312 is also preferably sufficiently flexible to allow the prongs 333 to spread apart from one another.

Figures 17A, 17B:
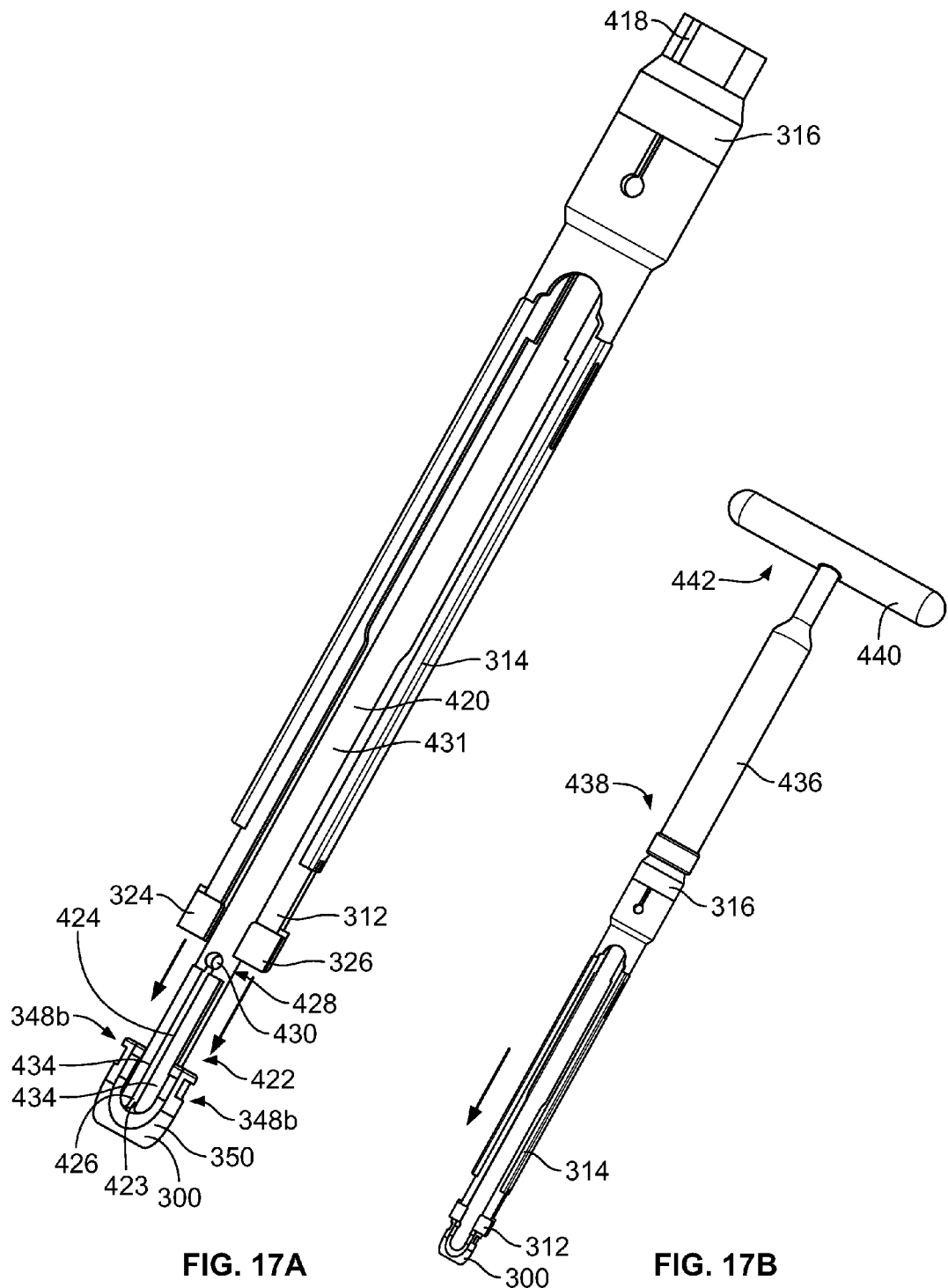
FIGS. 17A-D illustrate perspective views of portions of a method of using the blade rescue retractor of FIG. 11.
Figure 17C:
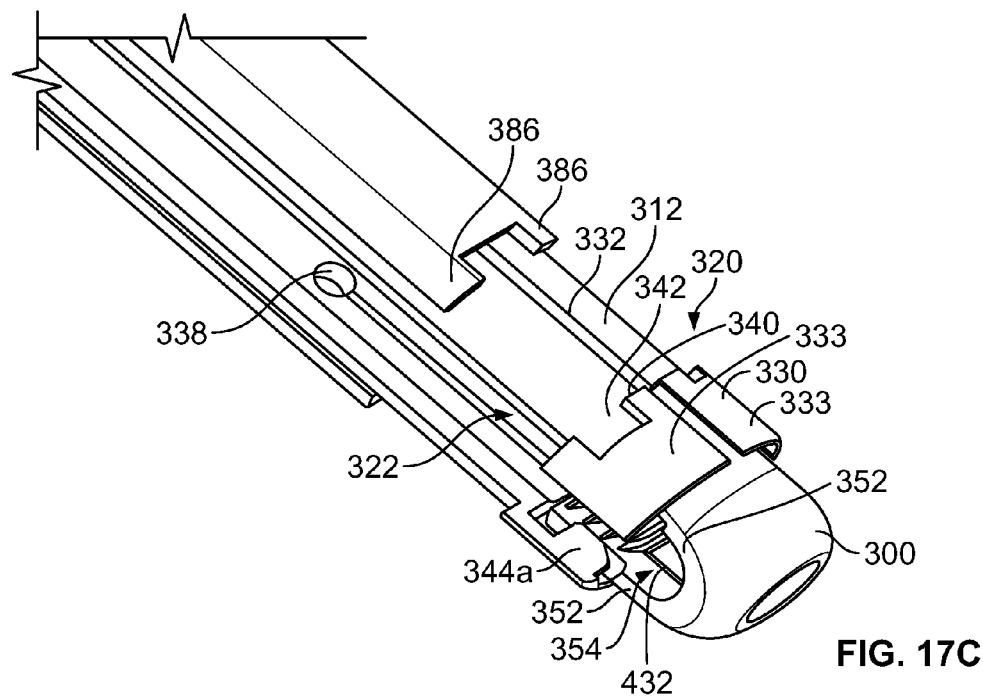
Figure 17D:
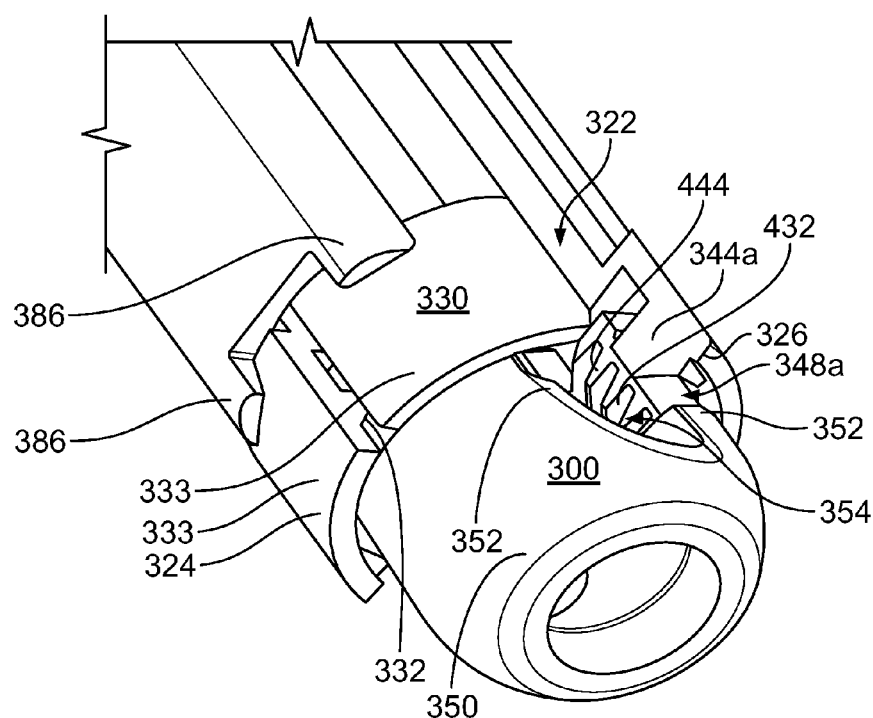

The gripping member 312 may include an engagement portion 330 at its distal end 320 for engaging the pedicle screw head 300, as shown in FIGS. 17C and 17D. The engagement portion 330 may be in the form of a collar protruding radially outward from the outer surfaces of the legs 324, 326. As shown in FIG. 13A, the proximal end of the engagement portion 330 may define a ledge 340 extending substantially transverse to the longitudinal axis of the gripping member 312. The ledge 340 may include one or more recesses 342 extending distally therefrom.

Figure 13B:
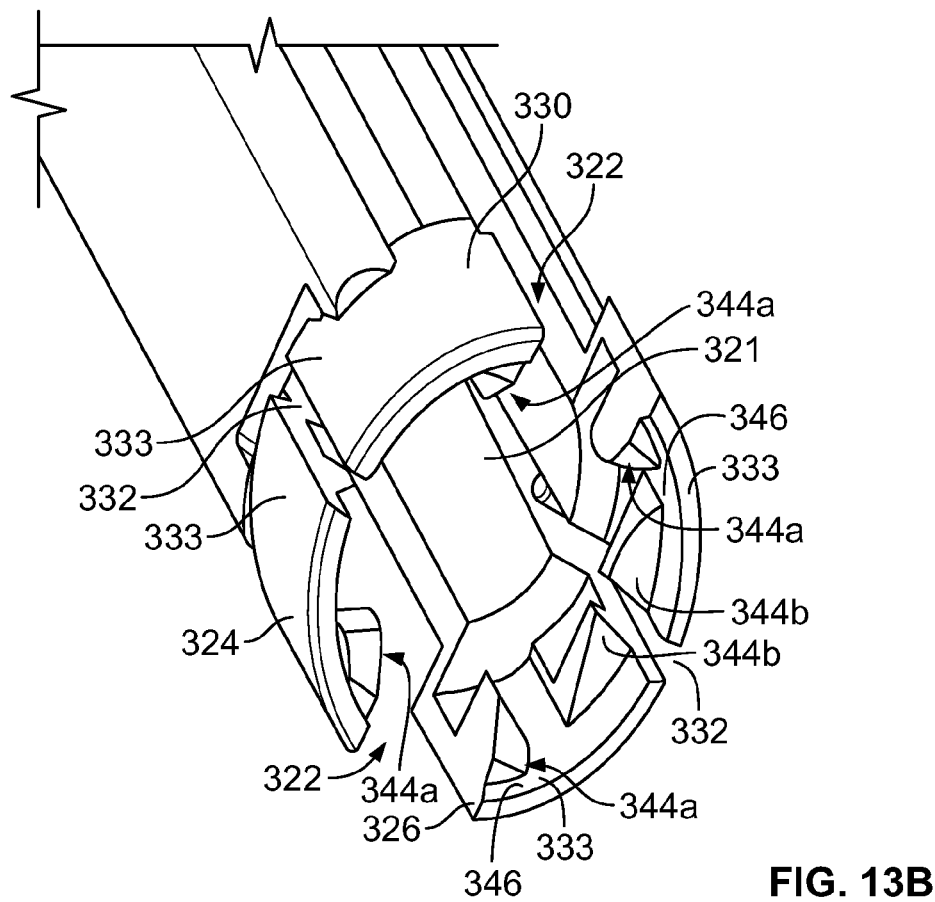
FIG. 13B illustrates a partial perspective view of the blade retractor system of FIG. 11.

FIG. 13B illustrates a perspective view of the engagement portion 330 showing the various structures for engaging the pedicle screw head 300. In particular, the engagement portion 330 preferably includes one or more tabs 344a,b projecting inwardly from an interior surface 346 of the engagement portion 330 and structured for engagement with corresponding structures on the exterior surface 350 of the pedicle screw head 300. For example, tabs 344a located on either side of the slots 322 between the legs 324, 326 may be sized to engage the pedicle screw head 300 along the edges 352 of the lateral openings 354 through which the fixation rod passes when it is seated within the pedicle screw heads 300 (see FIG. 17D). The pedicle screw head 300 may include recesses 348a along those edges 352 for receiving the tabs 344a of the engagement portion 330 (see FIG. 17D). Similarly, tabs 344b located on either side of the slots 332 of each leg 324, 326 may be sized to engage one or more recesses 348b (see FIG. 17A) in the exterior surface 350 of the pedicle screw head 300 between the lateral openings 354.

Figure 14:
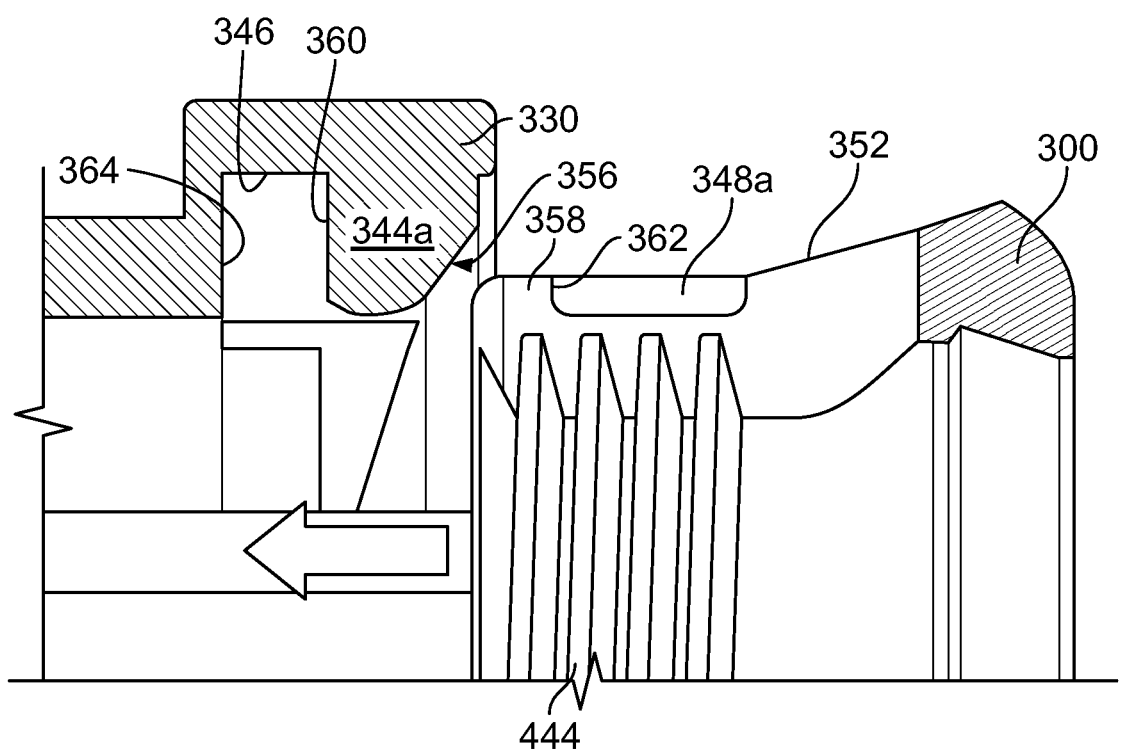
FIG. 14 illustrates a partial sectional view of the gripping member of FIG. 13 moving into engagement with a pedicle screw head.

Desirably, all of the tabs 344a,b have an angled chamfer 356 on their distal ends to ease insertion of the gripping member 312 and, in turn, the retractor 310 over the pedicle screw head 300. For example, as shown in FIG. 14, the chamfers 356 may be arranged such that, as the distal end 308 of the retractor 310 is moved distally over the proximal end 358 of the pedicle screw head 300, the chamfers 356 will cause the engagement portion 330 to spread apart. In particular, the chamfers 356 on tabs 344a will cause the prongs 333 to spread apart, and the chamfers 356 on tabs 344b will cause the legs 324, 326 to spread apart, such that the pedicle screw head 300 is received within the engagement portion 330. Further distal movement of the retractor 310 will move the tabs 344a,b into engagement with the corresponding recesses 348a,b of the pedicle screw head 300. Once the tabs 344a,b are seated within the recesses 348a,b, the engagement portion 330 is preferably structured to at least somewhat resist unwanted separation of the retractor 310 from the pedicle screw head 300. That is, lateral surfaces 360 on the proximal ends of the tabs 344a,b will engage lateral surfaces 362 at the proximal ends of the recesses 348a,b to prevent the retractor 310 from moving proximally and disengaging the pedicle screw head 300. Additionally, lateral surfaces 364 at the proximal end of the engagement portion 330 will engage the proximal end 358 of the pedicle screw head 300 to prevent the retractor 310 from moving distally with respect to the pedicle screw head 300.

Referring again to FIG. 13, an exterior surface 365 of the gripping member 312 between its proximal and distal ends 318, 320 may include one or more projections 366 extending laterally outward. In some embodiments, such projections may be in the form of generally cylindrical pins. Additionally, the proximal end 318 of the gripping member may include an externally threaded portion 368.

Figure 15:
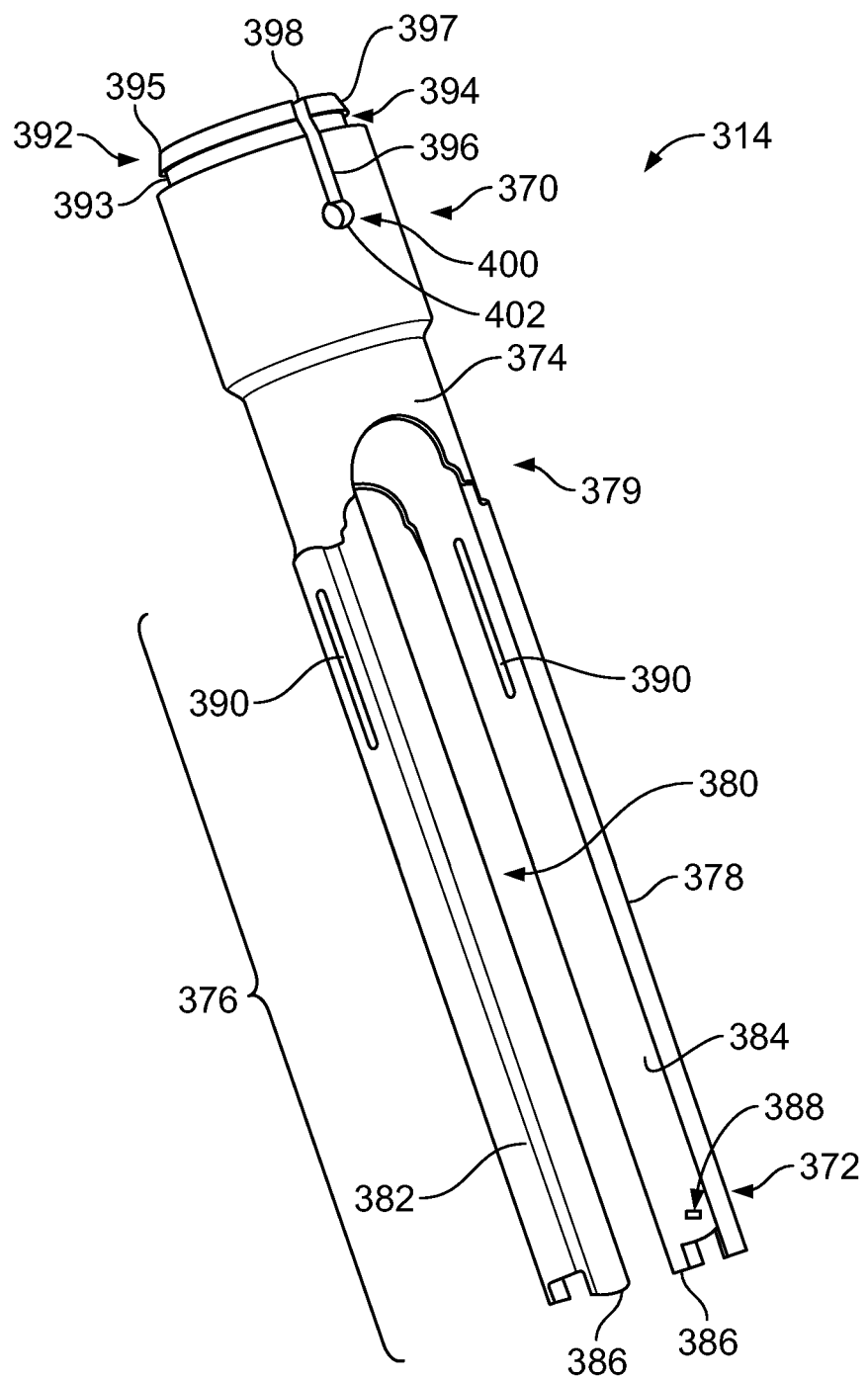
FIG. 15 illustrates a perspective view of a component of a locking member of the blade rescue retractor of FIG. 11.

FIG. 15 illustrates a perspective view of a portion of the locking member 314, separated from the gripping member 312, and with the actuation mechanism 316 removed. The locking member 314 has a proximal end 370 and a distal end 372. The locking member 314 may have a hollow, sleeve-like shape constructed to receive the gripping member 312 within its interior. The locking member 314 may have a generally tubular body portion 374 with first and second generally planar legs 376, 378 extending distally from its distal end 379, the legs 376, 378 defining a pass-through slot 380 between the legs 376, 378. In the embodiment illustrated in FIG. 15, the legs 374, 376 have exterior surfaces 382 that are substantially flat, while the interior surfaces 384 are generally curved so as to substantially match the exterior surface 365 of the gripping member 312. The locking member 314 may be symmetrical on either side of the pass-through slot 380, such that the legs 376, 378 have the same structure.

In some alternative embodiments, the entire locking member 314 may have a generally tubular shape similar to that of the gripping member 312 illustrated in FIG. 13, such that the legs 374, 376 of the locking member 314 are generally arcuate segments. In yet other embodiments, rather than being generally planar or generally arcuate, the legs 374, 376 may have a substantially smaller profile and may be in the form of rods extending distally from the body portion 374.

The interior surface 384 of the locking member 314 may include at least one or more projections 388 extending laterally inwardly, and preferably includes one such projection 388 located on each of the legs 376, 378. The projections 388 are preferably arranged to be received within the corresponding slots 332 in the legs 324, 326 of the gripping member 324. Such projections may be in the form of generally cylindrical pins. Desirably, when the locking member 314 is moved in the proximal direction, the projections 388 are shaped to cause the prongs 333 to spread apart as each projection 388 is moved proximally within the tapered slot 332.

The distal end 372 of the locking member 314 may include one or more distally extending projections 386 configured to be received within the corresponding recesses 342 in the engagement portion 330 of the gripping member 312. When engaged with the corresponding recesses 342, the projections 386 of the locking member may desirably restrain the prongs 333 of the gripping member 312 from spreading apart.

The locking member 314 may include one or more slots 390 arranged to receive the one or more projections 366 of the gripping member 312 therein. Desirably, the interaction between the projections 366 and the slots 390 constrains the movement of the locking member 314 with respect to the gripping member 312 to be substantially linear along the proximal and distal directions, while preventing either the locking member 314 or the gripping member 312 from rotating with respect to one another about the longitudinal axis of the retractor 310.

The proximal end 392 of the body portion 374 may include a connection 394 for engaging the actuation mechanism 316. The connection 394 may include an annular recess 393 extending around the circumference of the body portion 374 and an annular flange 395 positioned proximally of the recess 393. The annular flange 395 is preferably chamfered at its proximal end 397 to ease the connection of the actuation mechanism 316 to the body portion 374. The proximal end 370 of the locking member 314 also preferably includes at least one slot 396 extending distally from the proximal end 392 of the body portion 374. The slot 396 may have a proximal end 398 open to the proximal end 392 of the body portion 374 and a distal end 400 terminating at a hole 402. The hole may be rounded to reduce stress concentrations at the distal end 400 of the slot 396, and, desirably, the hole 402 may be circular. The slot 396 preferably allows the proximal end 392 of the body portion 374, and thus the connection 394, to deflect at least slightly inwardly so that the actuation mechanism 316 can be snapped on to the proximal end 392 of the body portion 374 and into engagement with the connection 394.

Figure 16A:
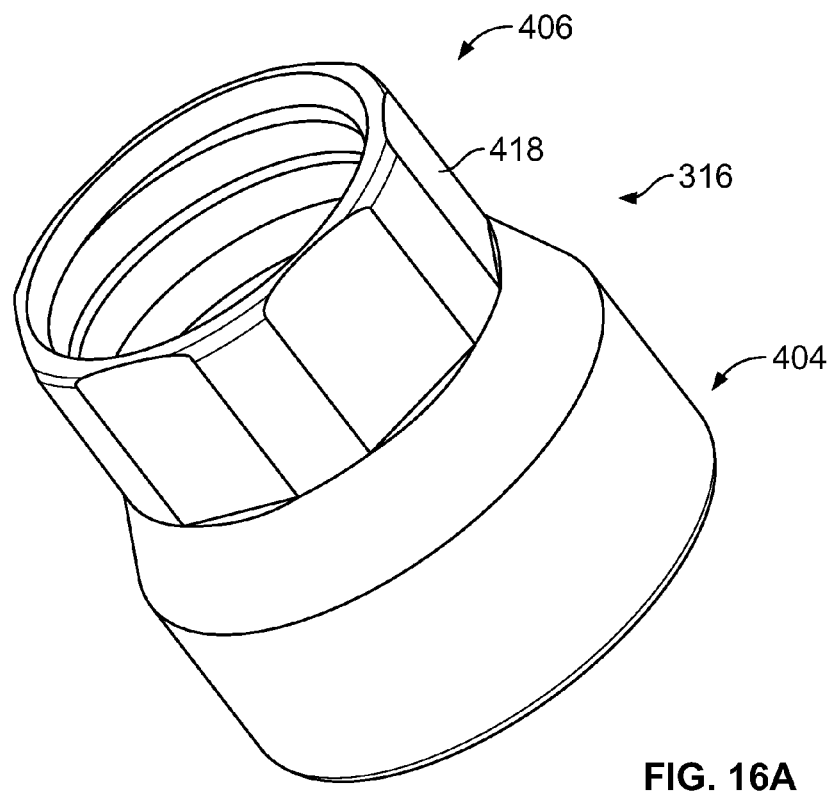
FIG. 16A illustrates a perspective view of another component of a locking member of the blade rescue retractor of FIG. 11.
Figure 16B:
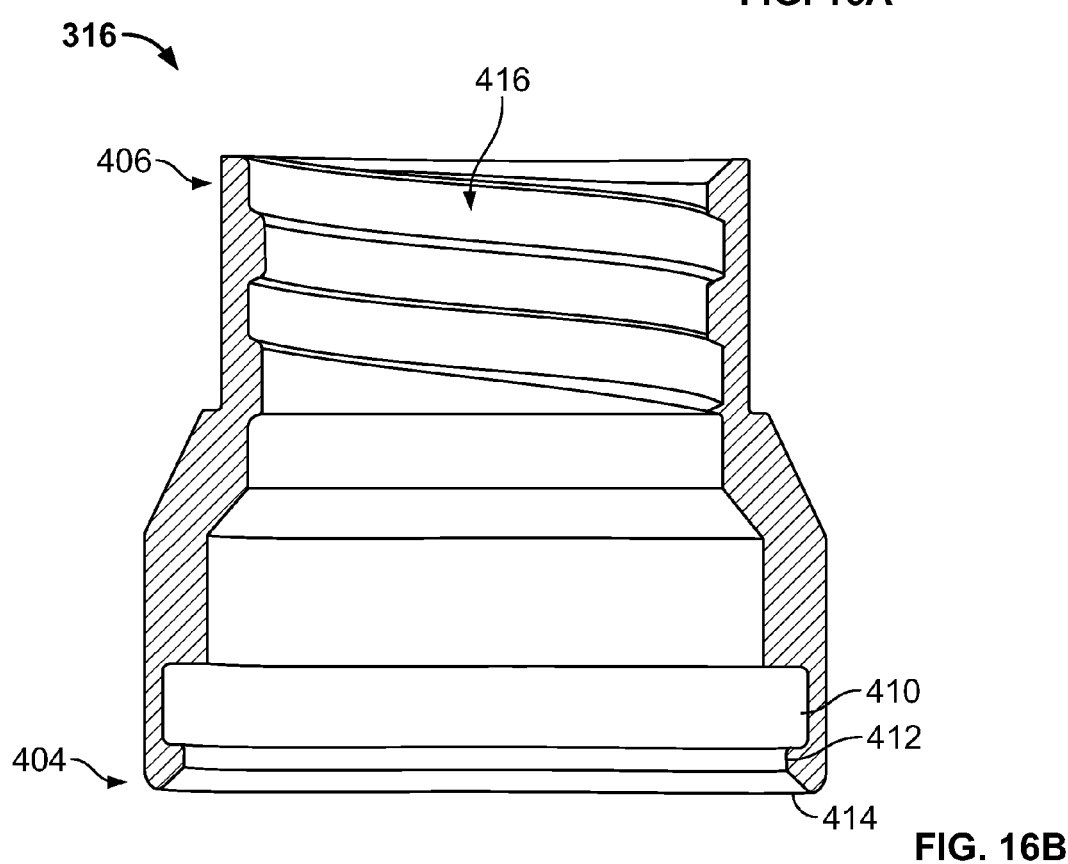
FIG. 16B illustrates a sectional view of the component FIG. 16B.

As shown in FIGS. 16A and 16B, one embodiment of the actuation mechanism 316 is in the form of a generally tubular sleeve. The actuation mechanism 316 has a distal end 404 and a proximal end 406. A connection 408, which is structured to engage the connection 394 at the proximal end 392 of the body portion 374, may be located in the interior of the actuation mechanism 316 at its distal end 404. The connection 408 may include an annular recess 410 extending around the circumference of the body portion 374 and an annular flange 412 positioned distally of the recess 410. The annular flange 412 is preferably chamfered at its distal end 414 to ease the connection of the actuation mechanism 316 to the body portion 374. The actuation mechanism 316 may thus be connected to the body portion 374 by fitting the distal end 404 of the actuation mechanism 316 over the proximal end 392 of the body portion 374 until the annular flange 412 of the actuation mechanism 316 is received within the annular recess 393 of the body portion 374 and the annular flange 395 of the body portion is received within the annular recess 410 of the actuation mechanism 316. That engagement desirably permits the actuation mechanism 316 to rotate with respect to the body portion 374 about the longitudinal axis of the retractor 310 while restraining the actuation mechanism 316 from separating from the body portion 374.

The actuation mechanism 316 desirably includes an internally threaded portion 416 configured to engage the externally threaded portion 368 of the gripping member 312 when the gripping member is received within the locking member 314. In that manner, rotation of the actuation mechanism 316 with respect to the body portion 374 of the locking member 314 will cause the locking member 314 to move in a proximal direction or a distal direction along the gripping member 312. That rotation is preferably driven by a tool removably engaged to a tool interface 418 at the proximal end 406 of the actuation mechanism 316. As shown in FIG. 16A, the tool interface 418 may comprise an external, hexagonally shaped interface configured to be received within a correspondingly shaped recess of the tool or engaged by a wrench or other appropriate tool. Alternatively, any other configuration of a tool interface known in the art may be used.

The locking member 314, and preferably at least the legs 376, 378 of the locking member 314, are desirably relatively rigid, while the gripping member 312 is desirably partially flexible, such that the legs 324, 326 and prongs 333 can spread apart from one another, as discussed above. In that manner, as discussed above, the flexibility of the legs 324, 326 and prongs 333 may permit the engagement portion 330 to spread apart when moved distally over the proximal end 358 of the pedicle screw head 300, after which the tabs 344a,b of the engagement portion 330 may become engaged with the recesses 348a,b of the pedicle screw head 300. Once the engagement portion 330 is engaged with pedicle screw head 300, the locking member 314 may help to rigidly secure the retractor 310 to the pedicle screw head 300 by preventing the gripping member 312 from becoming disengaged with the pedicle screw head 300. In particular, the locking member 314 may be advanced distally along the gripping member 312 from a retracted position towards a locked position, which causes the legs 376, 378 of the locking member 314 to move distally along the legs 324, 326 of the gripping member 312. In that manner, the relatively rigid legs 376, 378 of the locking member 314 preferably restrain the relatively flexible legs 324, 326 of the gripping member 312 from deflecting outwardly and thereby disengaging the pedicle screw head 300. In a similar manner, the relatively rigid legs 376, 378 of the locking member 314 also preferably restrain the prongs 333 of the gripping member 312 from spreading apart.

An exemplary method of using the blade rescue retractor 310 of FIGS. 11-16B is illustrated in FIGS. 17A-D. As shown, the use of the retractor 310 may be particularly desirable in cases where both blades of the blade screw have been removed and further access to the pedicle screw head 300 is desired. Such scenarios may arise, for example, where both blades of the blade-screw were intentionally or unintentionally removed (e.g., broken off at frangible portions) before it was determined that further revision may be necessary.

In order to help move the retractor 310 into engagement with the pedicle screw head 300, an elongate guide tool 420 may first be inserted through a skin incision and distally into engagement with the pedicle screw head 300. The guide tool 420 may include an engagement portion 422 at its distal end 423 for stable engagement with the pedicle screw head 300. In the embodiment illustrated in FIG. 17A, the engagement portion 422 may comprise a slot 424 extending proximally from the distal end 423 of the guide tool 420. The slot 424 may have a distal end 426 open to the distal end 423 of the guide tool 420 and a proximal end 428 terminating at a hole 430. The hole may be rounded to reduce stress concentrations at the proximal end 428 of the slot 424, and, desirably, the hole 430 may be circular. The slot 424 may allow the engagement portion 422 to deflect at least slightly inwardly. The outer surface 431 of the guide tool 420 is preferably slightly larger than the interior dimension of the rod receiving surface 432 (see FIGS. 17C and 17D) in the pedicle screw head 300, such that the engagement portion 422 may deflect slightly inwardly upon being received within the rod receiving surface 432, so as to stabilize the engagement between the engagement portion 422 and the rod receiving surface 432. The engagement portion 422 may also include one or more laterally extending projections 434, which may be sized to be received within the lateral openings 354 of the pedicle screw head 300, to further stabilize the engagement between the engagement portion 422 and the pedicle screw head 300. Desirably, the outer surface 431 of the guide tool 420 proximal of the engagement portion 422 is sized to be relatively closely received within the interior surface 321 of the gripping member 312.

After the guide tool 420 is moved into engagement with the pedicle screw head 300, the retractor 310 may be advanced distally along the guide tool 420 towards the pedicle screw head 300, preferably with the locking member 314 in a retracted position, as shown in FIG. 17A. The retractor 310 may be advanced until the engagement portion 330 of the gripping member 312 moves over and into engagement with the pedicle screw head 300, after which the locking member 314 may be advanced distally from the retracted position (as shown in FIG. 17C) to a locked position (as shown in FIG. 17D), in order to restrain the engagement portion 330 of the gripping member 312 from spreading apart and becoming disengaged with the pedicle screw head 300. In order to advance the locking member distally towards the locked position, a tool 436 may be engaged with the tool interface 418 at the proximal end 406 of the actuation mechanism 316, as shown in FIG. 17B. The tool 436 may include a recess (not shown) at its distal end 438 for receiving the tool interface 418, and the tool 436 may include a handle 440 at its proximal end 442 for providing a gripping surface and also, preferably, leverage for rotating the tool 436 to drive the actuation mechanism 316.

Once the retractor 310 is securely engaged to the pedicle screw head 300, the retractor 310 may be used in much the same manner as the retractor 60 of FIGS. 4-8B. That is, if both blades were broken off before the fixation rod was inserted, the rod may be inserted using the retractor 310 as a functional replacement for the blade-screw having the missing blades. That is, the first and second legs 324, 326 of the gripping member 312, stabilized by the first and second legs 376, 378 of the locking member 314, desirably act as replacements for the missing blades by holding back the surrounding tissue, such that the retractor 310 provides a pathway through the tissue from the respective pedicle screw head 300 to the incision associated with that pedicle screw. Moreover, the slots 322 between the legs 324, 326 of the gripping member 312 are analogous to the openings between the blades of the blade-screws, as the slots 322 of the gripping member 312 allow the fixation rod to extend transverse to the longitudinal axis of the retractor 310 and be guided towards the pedicle screw heads 300.

After the fixation rod has been positioned within the body extending between one or more blade screws and/or retractors 160 (as shown in FIGS. 4-8B) and/or retractors 310, the rod may then be persuaded towards and into the rod receiving surfaces 432 of the pedicle screw heads 300. That may involve use of a persuader (not shown) in much the same manner as the persuader 80 illustrated in FIGS. 4 and 7-8B, which persuader may be sized and shaped to be positioned over the retractor 310 and advanced distally to persuade a transversely oriented rod towards the pedicle screw head 300. A blocker inserter with blocker may also be used and positioned within the longitudinal pathway 311 of the retractor 310 through the opening 313 at its proximal end 309. In embodiments of the retractor 310 having a threaded portion along a portion of the interior surface 321 of the gripping member 312, the blocker (not shown) may be engaged with the threads of such threaded portion and rotated to advance the blocker along the threaded portion and into engagement with the threads 444 (see FIG. 17D) in the rod receiving surface 432 of the pedicle screw head 300.

Once the blocker is finally tightened within rod receiving surface 432 of the pedicle screw head 300, thus capturing and securing the rod within the screw head 300, the blocker inserter 201 and persuader 180 may be removed from the body. Thereafter, the retractor 310 may be removed. In order to remove the retractor 310, the locking member 314 may first be moved proximally into the retracted position, such as by rotation of the actuation mechanism 316 with the tool 436. As discussed above, the proximal movement of the locking member 314 may cause the projections 388 of the locking member 314 to move proximally within the tapered slots 332 of the gripping member 312, thus spreading apart the prongs 333 of the gripping member 312. Even with the prongs 333 spread apart, however, twisting of the retractor 310 about its longitudinal axis may be necessary to cause the engagement portion 300 to further spread apart and disengage tabs the tabs 344a,b from the recesses 348a,b in the pedicle screw head 300, so that the retractor 310 can be removed. After all of the desired components have been removed from the body, the incisions through which the blade screws, retractors 310, and other components of the blade rescue system extended may then be closed.

Figure 18:
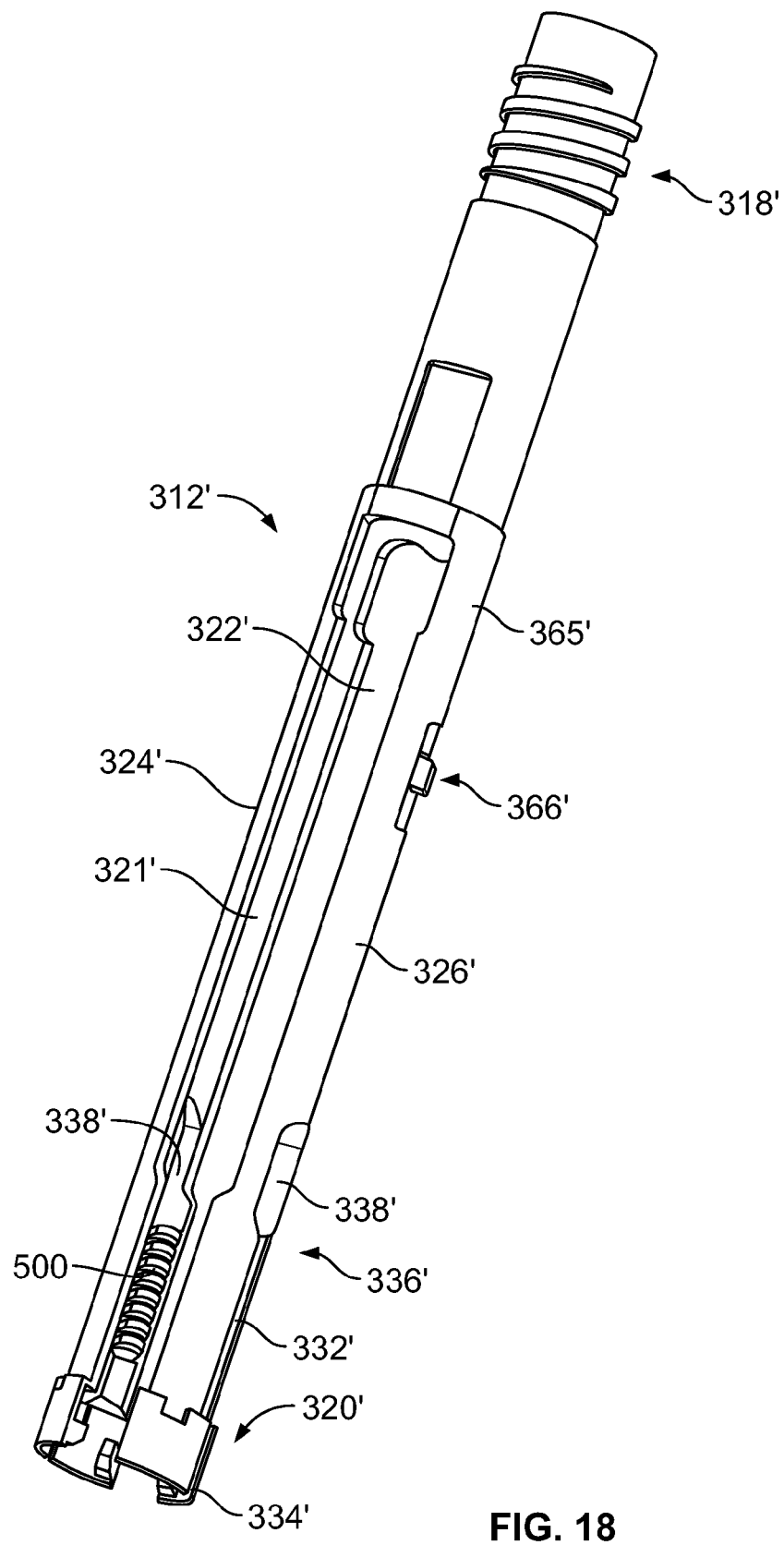
FIG. 18 illustrates a perspective view of a gripping member of a blade rescue retractor in accordance with another embodiment of the present invention.
Figure 19:
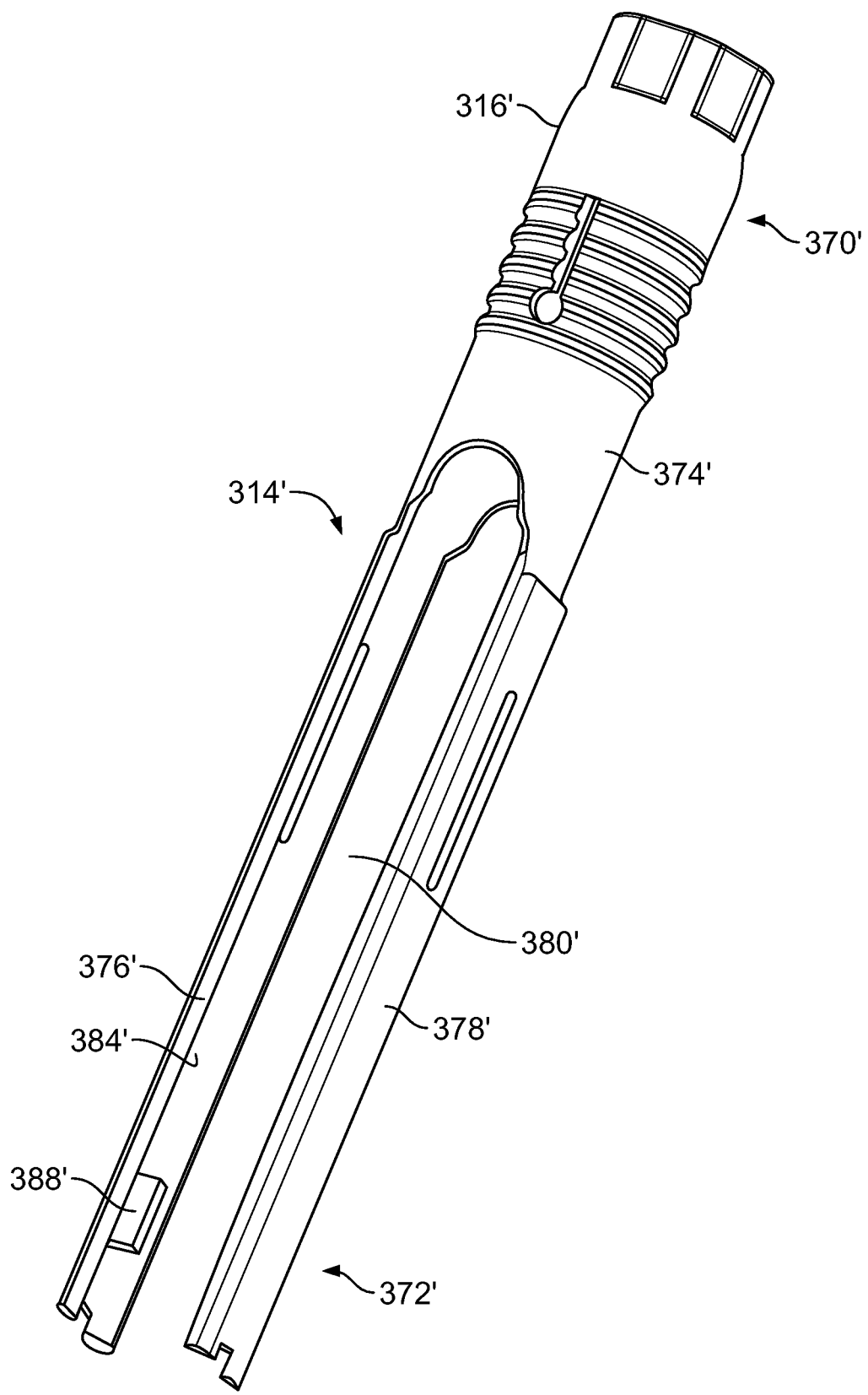
FIG. 19 illustrates a perspective view of a locking member of a blade rescue retractor in accordance with another embodiment of the present invention.

FIGS. 18 and 19 illustrate alternative embodiments of a gripping member 312' and a locking member 314' (with actuation mechanism 316'), which are largely similar to those illustrated in FIGS. 13 and 15, respectively, and in which like reference numerals refer to like elements. Among the differences from the gripping member 312 of FIG. 13, the gripping member 312' of FIG. 18 includes a threaded portion 500 along its inner surface 321' near the distal end 320'. The threaded portion 500 may be constructed for engagement with an externally threaded blocker so as to advance that blocker towards and into the pedicle screw head, as discussed above in connection with the embodiments illustrated in FIGS. 8B and 10. Also in the embodiment of FIG. 18, the holes 338' at the proximal ends 336' of the slots 332' in each of the legs 324', 326' have an elongated shape. In particular, the holes 338' may have a generally elliptical shape having a major diameter extending substantially along the longitudinal axis of the gripping member 312'. The projections 366' along the exterior surface 365' of the gripping member 312' of the embodiment of FIG. 18 also may have an elongated shape. For example, the projections 366' may be elongated substantially along the longitudinal axis of the gripping member 312'. Among the differences from the locking member 314 of FIG. 15 are the shape of the projections 388' extending inwardly from the interior surface 384' for engagement with the slots 332' of the gripping member 312'. In particular, the projections 388' may have an elongated shape (e.g., elongated substantially along the longitudinal axis of the locking member 314').

In an alternative embodiment of a locking member (not shown) for use in a blade rescue retractor like that illustrated in FIGS. 11-19, the locking member need not extend substantially along the entire length of the gripping member in locked position. Such an embodiment of the locking member may not include legs, and the tubular body portion may instead be structured to extend at least partially along the legs 324, 326 of the gripping member 312 in the locked position, so as to restrain the legs 324, 326 of the gripping member 312 from deflecting outwardly and disengaging the pedicle screw head 300.

In a further alternative embodiment of a blade rescue retractor (not shown) like that illustrated in FIGS. 11-19, the locking member and gripping member may instead be structured so that the locking member is received within the gripping member. In such an embodiment, the engagement between the locking member and the gripping member may be such that, when the locking member is in the locked position, the locking member restrains the legs of the gripping member from deflecting outwardly and disengaging the pedicle screw head 300. For example, the gripping member may include a structure such as an internal track for receiving the legs, or some other engagement structure on the legs, of the locking member. In yet a further embodiment of a blade rescue retractor (not shown), the legs of the locking member may be structured as stiffening members which are received within and movable along channels formed inside the legs (i.e., between the interior and exterior surfaces of the gripping member).

Although the blade rescue systems and methods of use above were described in connection with integrated blade-screws in which one or both blades had been broken off (e.g., broken at the frangible portions), such blade rescue systems could also be used in connection with other types of percutaneous access devices (such as those described in the '355 patent or the '798 patent) after such percutaneous access devices have been removed or have failed. For example, the blade rescue retractor 60 discussed in connection with FIGS. 4-8B could be used with a system having blades separately formed from and detachably connectable to the pedicle screw heads, as described in the '798 patent, and in which one of the blades has become disconnected to the associated pedicle screw head. Similarly, the blade rescue retractor 310 discussed in connection with FIGS. 11-17D could also be used with a similar system of separately formed blades in which both blades have become disconnected from the pedicle screw head.

In some alternative arrangements of any of at least the coupling, the retractor, the gripping member, the locking member, and the persuader as described previously herein, where either or all of bosses, projections, and protuberances are described as interfacing with holes, slots, or recesses, such holes, slots, or recesses and either or all of the bosses, projections, and protuberances corresponding to, being inserted in, or being engaged with the respective holes, slots, or recesses may be reversed such that they are on the other feature than that previously described herein. In some arrangements, where either or both of bosses and protuberances are described as being from flexible tabs or arms, such bosses and protuberances may simply extend from a wall, an inner perimeter, or body that may be rigid or inflexible.

It is to be understood that the disclosure set forth herein includes all possible combinations of the particular features described. For example, where a particular feature is disclosed in the context of a particular aspect, arrangement, configuration, or embodiment, or a particular claim, that feature can also be used, to the extent possible, in combination with and/or in the context of other particular aspects, arrangements, configurations, and embodiments of the invention, and in the invention generally.

Furthermore, although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An access device for percutaneously accessing a pedicle fastener connected to a vertebra of a patient, the access device comprising:
an elongate gripping member including a body portion, a first leg, and a second leg, the first and second legs each having a proximal portion connected to the body portion and a distal portion for engagement with a head of a pedicle fastener, the distal portion of the first leg including a first prong and a second prong, and the distal portion of the second leg including a third prong and a fourth prong, the first and second prongs having a first longitudinal slot therebetween permitting the first and second prongs to spread apart from one another, and the third and fourth prongs having a second longitudinal slot therebetween permitting the third and fourth prongs to spread apart from one another, wherein the distal portions of the first and second legs are deflectable away from one another to engage and disengage the head of the pedicle fastener, and wherein the first and second legs of the gripping member define a first pass-through slot therebetween, the first pass-through slot adapted to receive a spinal fusion rod therethrough; and
an elongate locking member connected to and movable relative to the gripping member between a retracted position and a locked position, wherein the locking member prevents the first and second legs of the gripping member from deflecting away from one another when in the locked position;
wherein the access device includes at least one projection arranged within the first slot, and wherein the projection is adapted to move along the first slot to cause the first and second prongs to spread apart from one another.

2. The access device of claim 1, wherein the projection is connected to the locking member, and wherein movement of the locking member to the retracted position causes the projection to move along the first slot so as to deflect the first and second prongs away from one another.

3. The access device of claim 1, further comprising at least one tab arranged to be received within a recess in the gripping member, wherein movement of the locking member to the locked position causes the tab to move into the recess.

4. The access device of claim 3, wherein the elongate locking member has a first extension aligned along the first leg and a second extension aligned along the second leg, and wherein the first and second extensions of the locking member prevent the respective first and second legs of the gripping member from deflecting away from one another when in the locked position, and wherein the tab is located at a distal end of the first extension.

5. The access device of claim 4, wherein the tab extends in a distal direction from the distal end of the first extension.

6. The access device of claim 5, wherein the recess extends distally within a ledge, the ledge protruding outwardly from an outer surface of the first leg.

7. The access device of claim 3, wherein engagement of the tab within the recess restrains movement of the first and second prongs away from one another.

8. The access device of claim 7, wherein the recess is located on one of the first and second prongs.

9. The access device of claim 1, wherein the gripping member is received within the locking member.

10. The access device of claim 9, wherein the gripping member has a tubular shape defining a longitudinal pathway therein along a central longitudinal axis of the access device.

11. The access device of claim 1, wherein the locking member is movable along a central longitudinal axis of the access device relative to the gripping member between the retracted and locked positions.

12. The access device of claim 11, further comprising an actuation mechanism for actuating movement of the locking member relative to the gripping member along the central longitudinal axis between the retracted and locked positions, wherein the actuation mechanism is adapted to actuate the movement of the locking member relative to the gripping member in response to rotation of the actuation mechanism.

13. The access device of claim 12, wherein the rotation of the actuation mechanism is about the central longitudinal axis of the access device.

14. The access device of claim 12, wherein the rotation of the actuation mechanism is along a threaded connection.

15. The access device of claim 1, wherein the elongate locking member has a first extension aligned along the first leg and a second extension aligned along the second leg, and wherein the first and second extensions of the locking member prevent the respective first and second legs of the gripping member from deflecting away from one another when in the locked position.

16. The access device of claim 15, wherein the first and second extensions of the locking member define a second pass-through slot therebetween, the second pass-through slot adapted to receive the spinal fusion rod therethrough, and wherein the first and second pass-through slots are aligned with one another about a central longitudinal axis of the access device.

17. A percutaneous spinal fusion system comprising:
the access device of claim 1; and
the pedicle fastener, wherein the pedicle fastener includes a first blade and a second blade detachably connected thereto, the first and second blades each having a plurality of holes spaced apart along a length of the respective blades.

18. A system for percutaneously accessing a pedicle fastener connected to a vertebra of a patient, the pedicle fastener having a head defining a receptacle for receiving a spinal fixation rod therein, and the pedicle fastener having two blades detachably connected to the head, comprising:

the access device of claim 1, for use when both of the blades become detached from the head; and a second access device for use when one of the blades becomes detached from the head, leaving a remaining blade, the second access device including an elongate body having a distal end for engagement with the head of the pedicle fastener, the body defining a longitudinal bore therein along a central longitudinal axis of the body, and the body including a groove therein extending longitudinally along the bore, the groove dimensioned to receive the remaining blade of the pedicle fastener therein.

19. An access device for percutaneously accessing a pedicle fastener connected to a vertebra of a patient, the access device comprising:

an elongate gripping member including a body portion, a first leg, and a second leg, the first and second legs each having a proximal portion connected to the body portion and a distal portion for engagement with a head of a pedicle fastener, the distal portion of the first leg including a first prong and a second prong, and the distal portion of the second leg including a third prong and a fourth prong, the first and second prongs having a first longitudinal slot therebetween permitting the first and second prongs to deflect relative to each other, and the third and fourth prongs having a second longitudinal slot therebetween permitting the third and fourth prongs to deflect relative to each other, wherein the distal portions of the first and second legs are deflectable away from one another to engage and disengage the head of the pedicle fastener; and an elongate locking member connected to and movable relative to the gripping member between a retracted position and a locked position, wherein the locking member prevents the first and second legs of the gripping member from deflecting away from one another when in the locked position, the locking member having a projection connected thereto, the projection being arranged within the first slot, wherein movement of the locking member to the retracted position causes the projection to move along the first slot so as to deflect the first and second prongs away from one another.

20. The access device of claim 19, further comprising at least one tab arranged to be received within a recess in the gripping member, wherein movement of the locking member to the locked position causes the tab to move into the recess.

21. The access device of claim 20, wherein engagement of the tab within the recess restrains movement of the first and second prongs away from one another.

22. The access device of claim 19, wherein the elongate locking member has a first extension aligned along the first leg and a second extension aligned along the second leg, and wherein the first and second extensions of the locking member prevent the respective first and second legs of the gripping member from deflecting away from one another when in the locked position.

23. A percutaneous spinal fusion system comprising:

the access device of claim 19; and the pedicle fastener, wherein the pedicle fastener includes a first blade and a second blade detachably connected thereto, the first and second blades each having a plurality of holes spaced apart along a length of the respective blades.

* * * * *